(12) United States Patent
Bindayel

(10) Patent No.: US 10,390,904 B2
(45) Date of Patent: *Aug. 27, 2019

(54) ORTHODONTIC SYSTEMS

(71) Applicant: Naif Bindayel, Riyadh (SA)

(72) Inventor: Naif Bindayel, Riyadh (SA)

(*) Notice: Subject to any disclaimer, the term of this patent is extended or adjusted under 35 U.S.C. 154(b) by 187 days.

This patent is subject to a terminal disclaimer.

(21) Appl. No.: 15/160,337

(22) Filed: May 20, 2016

(65) Prior Publication Data

US 2017/0128168 A1    May 11, 2017

Related U.S. Application Data

(60) Provisional application No. 62/252,760, filed on Nov. 9, 2015.

(51) Int. Cl.

| A61C 7/12 | (2006.01) |
|---|---|
| A61B 90/98 | (2016.01) |
| A61C 7/20 | (2006.01) |
| A61C 7/00 | (2006.01) |
| A61C 7/14 | (2006.01) |
| A61C 7/22 | (2006.01) |
| A61C 7/28 | (2006.01) |

(Continued)

(52) U.S. Cl.
CPC ............ *A61B 90/98* (2016.02); *A61B 5/4547* (2013.01); *A61B 5/6802* (2013.01); *A61C 7/002* (2013.01); *A61C 7/12* (2013.01); *A61C 7/14* (2013.01); *A61C 7/20* (2013.01); *A61C 7/22* (2013.01); *A61C 7/28* (2013.01); *A61B 5/0022* (2013.01); *A61B 2090/064* (2016.02); *A61B 2560/0219* (2013.01); *A61B 2560/045* (2013.01); *A61B 2562/0252* (2013.01)

(58) Field of Classification Search
CPC .. A61C 7/002; A61C 7/12; A61C 7/14; A61C 7/20; A61C 7/22; A61C 7/28; A61B 90/98; A61B 2090/064; A61B 2560/0219; A61B 2560/045
See application file for complete search history.

(56) References Cited

U.S. PATENT DOCUMENTS

| 4,243,387 A | 1/1981 | Prins |
|---|---|---|
| 4,292,025 A | 9/1981 | Förster |
| 5,032,080 A | 7/1991 | Hakansson et al. |

(Continued)

FOREIGN PATENT DOCUMENTS

WO    WO 03/096922    * 11/2003    ............... A61C 7/14

OTHER PUBLICATIONS

Translation of WO 03/096922 retreived from https://patentscope.wipo.int/search/en/detail.jsf?docId=WO2003096922&recNum=1&maxRec=&office=&prevFilter=&sortOption=&queryString=&tab=PCTDescription on May 17, 2018.*

(Continued)

*Primary Examiner* — Heidi M Eide
(74) *Attorney, Agent, or Firm* — Fish & Richardson P.C.

(57) ABSTRACT

An orthodontic system includes at least one orthodontic bracket attached to a surface of a tooth, in which the bracket define an archwire slot for receiving an archwire. The bracket includes a gear system, a motor to drive the gear system, and an integrated circuit to control the motor. A computer server sends instructions to the integrated circuit in the orthodontic bracket, and the integrated circuit controls the motor according to the instructions to drive the gear system to apply a force to the archwire.

29 Claims, 26 Drawing Sheets

(51) Int. Cl.
*A61B 5/00* (2006.01)
*A61B 90/00* (2016.01)

(56) References Cited

U.S. PATENT DOCUMENTS

| | | | |
|---|---|---|---|
| 5,035,614 A | 7/1991 | Greenfield | |
| 5,876,206 A | 3/1999 | Maurer | |
| 5,954,502 A | 9/1999 | Tuenge et al. | |
| 6,632,088 B2 | 10/2003 | Voudouris | |
| 7,306,458 B1 | 12/2007 | Lu | |
| 7,581,714 B2 | 9/2009 | Machu | |
| 9,531,237 B2 | 12/2016 | Miller | |
| 2001/0029008 A1 | 10/2001 | Jordan et al. | |
| 2003/0031975 A1* | 2/2003 | Voudouris | A61C 7/12 433/8 |
| 2003/0152889 A1* | 8/2003 | Uji | A61C 13/0024 433/169 |
| 2005/0026102 A1* | 2/2005 | Miller | A61C 7/00 433/24 |
| 2005/0269821 A1 | 12/2005 | Nadel et al. | |
| 2006/0074431 A1 | 4/2006 | Sutton et al. | |
| 2007/0184399 A1 | 8/2007 | Salich | |
| 2008/0248439 A1 | 10/2008 | Griffith et al. | |
| 2009/0286195 A1 | 11/2009 | Sears et al. | |
| 2009/0317757 A1 | 12/2009 | Lemchen | |
| 2012/0148973 A1 | 6/2012 | Johnston | |
| 2014/0134562 A1 | 5/2014 | Wu et al. | |
| 2014/0272751 A1 | 9/2014 | Cosse et al. | |
| 2015/0305833 A1* | 10/2015 | Cosse | A61C 7/002 433/3 |

OTHER PUBLICATIONS

Final Office Action for U.S. Appl. No. 15/160,255 dated Aug. 29, 2017.
International Search Report and Written Opinion of the International Searching Authority for International Application No. PCT/IB2016/056759 dated Apr. 4, 2017.
Non-Final Office Action for U.S. Appl. No. 15/160,234 dated Apr. 10, 2017.
Non-Final Office Action for U.S. Appl. No. 15/160,255 dated Apr. 5, 2017.
Non-Final Office Action for U.S. Appl. No. 15/160,291 dated Apr. 7, 2017.
Non-Final Office Action for U.S. Appl. No. 15/160,291 dated Jun. 8, 2018.
Non-Final Office Action for U.S. Appl. No. 15/160,277 dated Jul. 18, 2018.

\* cited by examiner

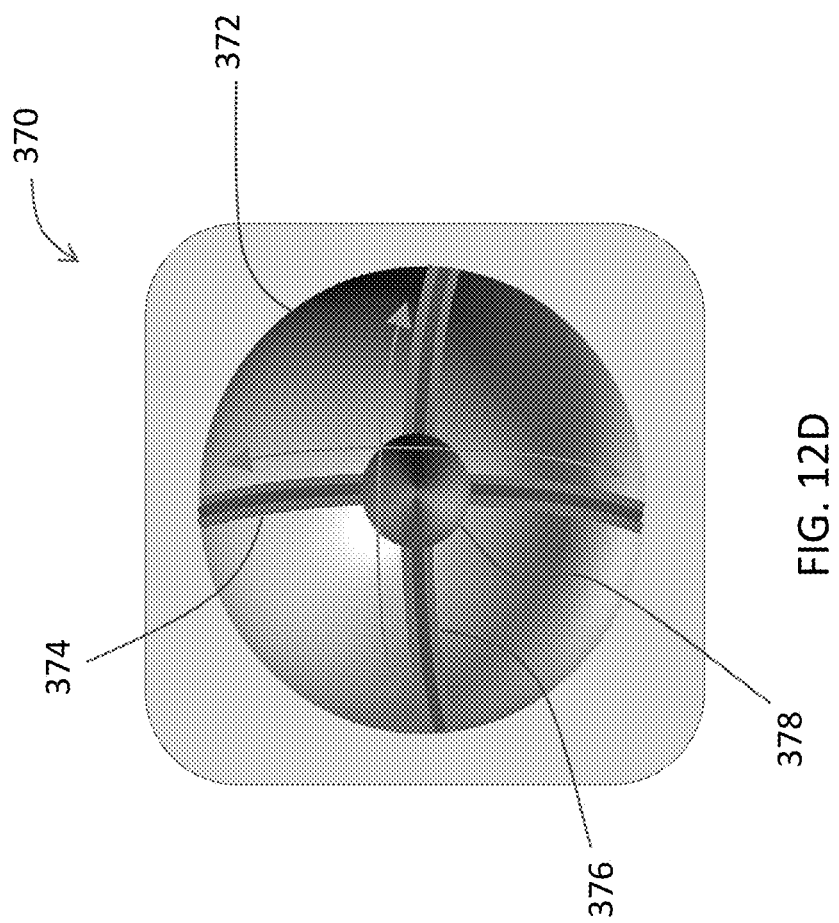

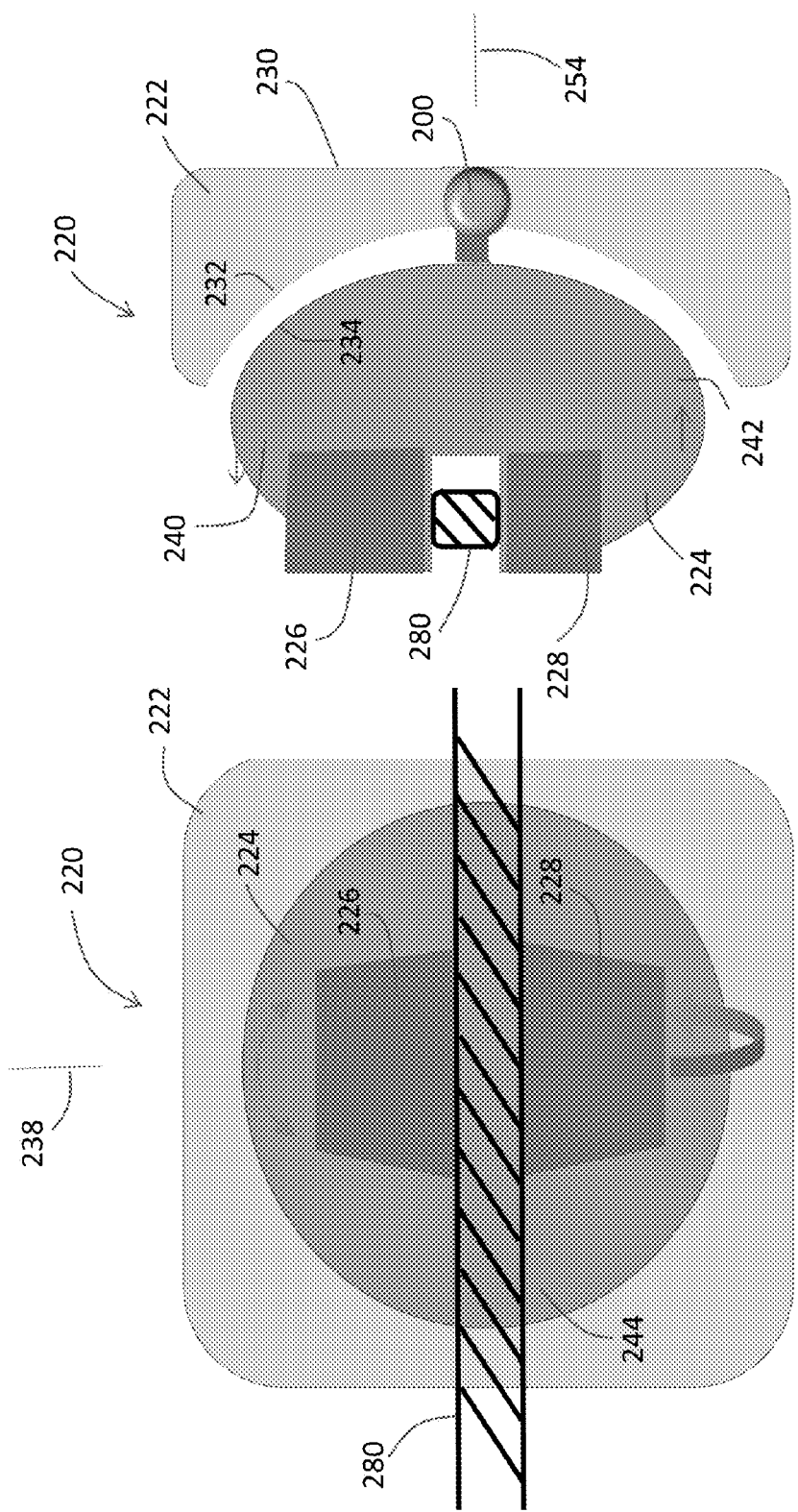

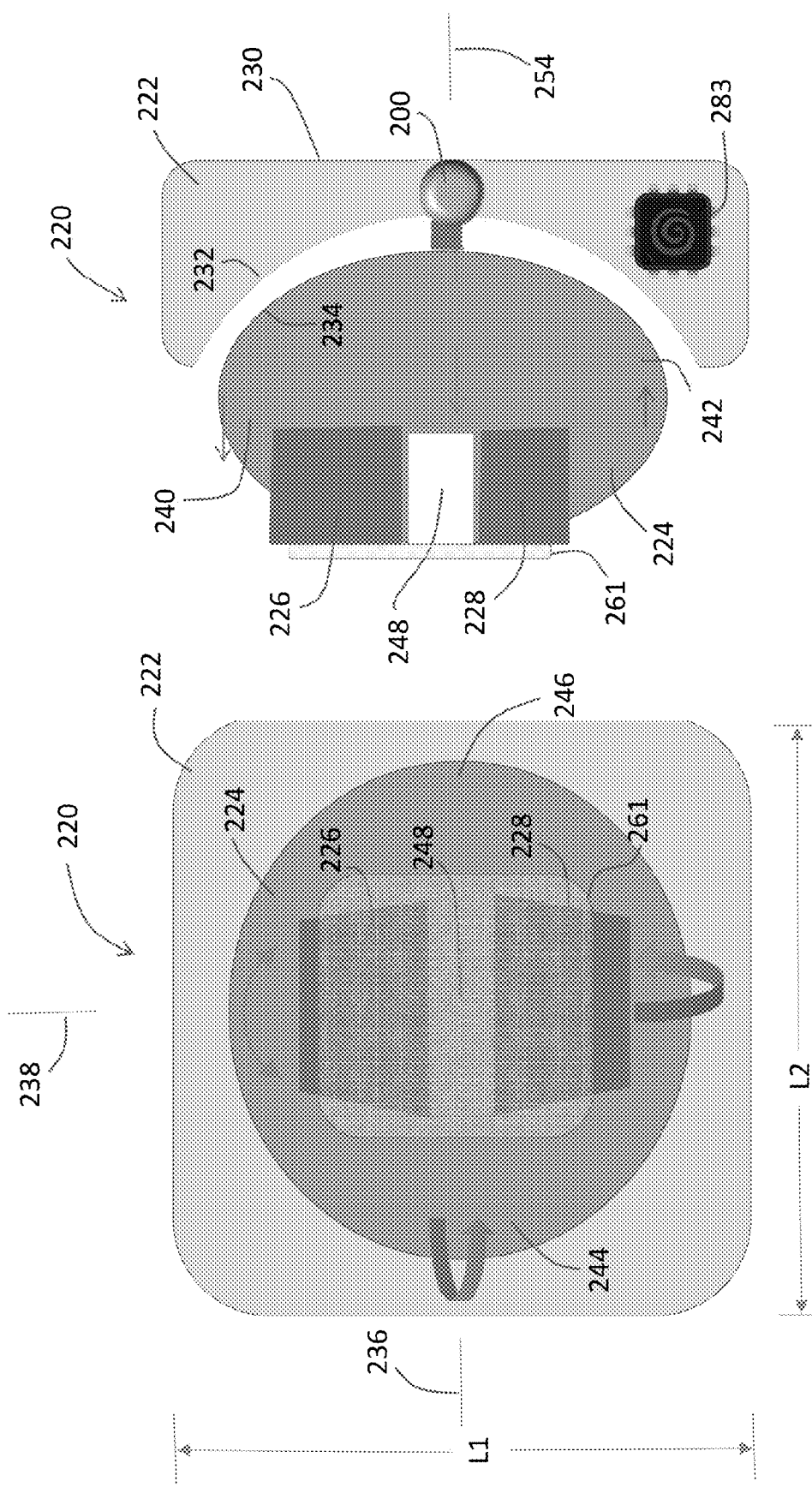

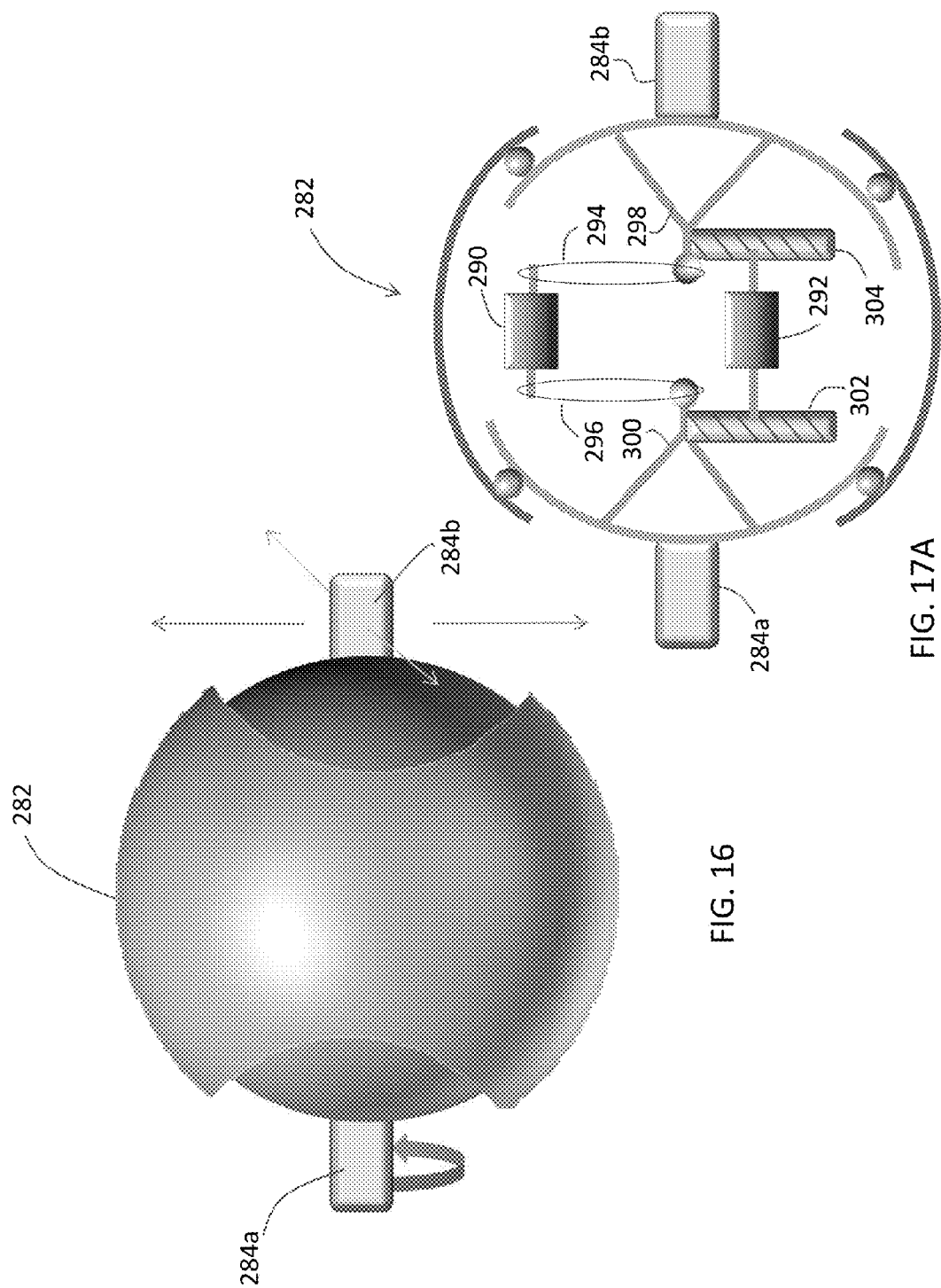

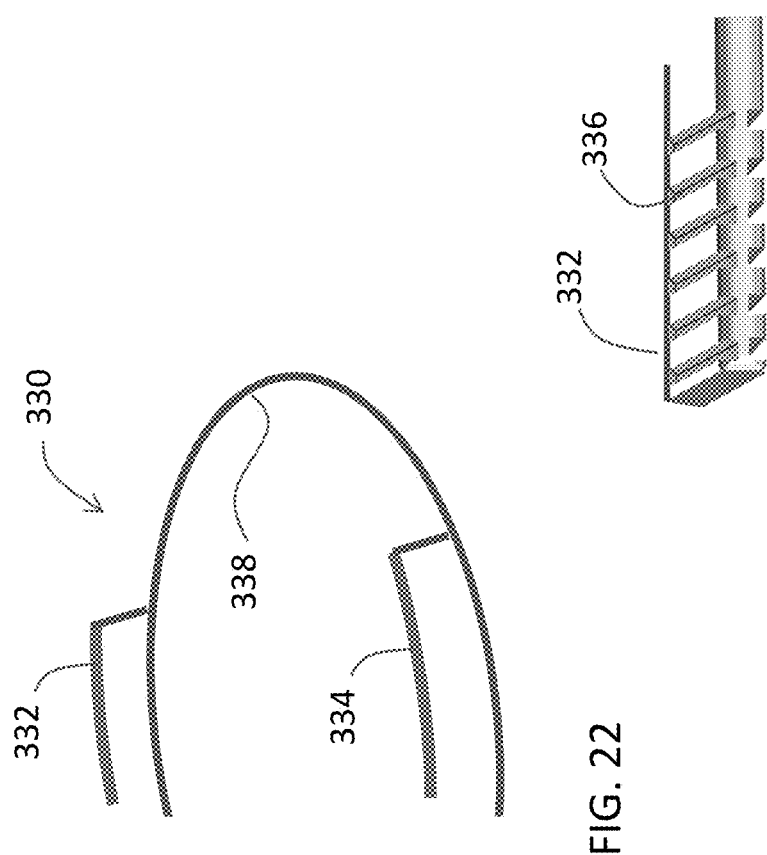
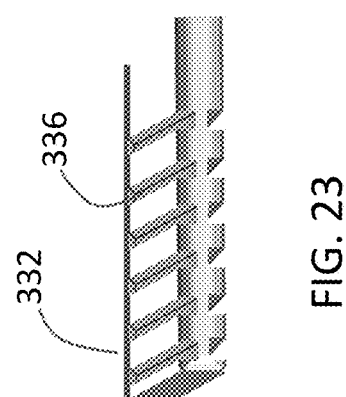
FIG. 22
FIG. 23

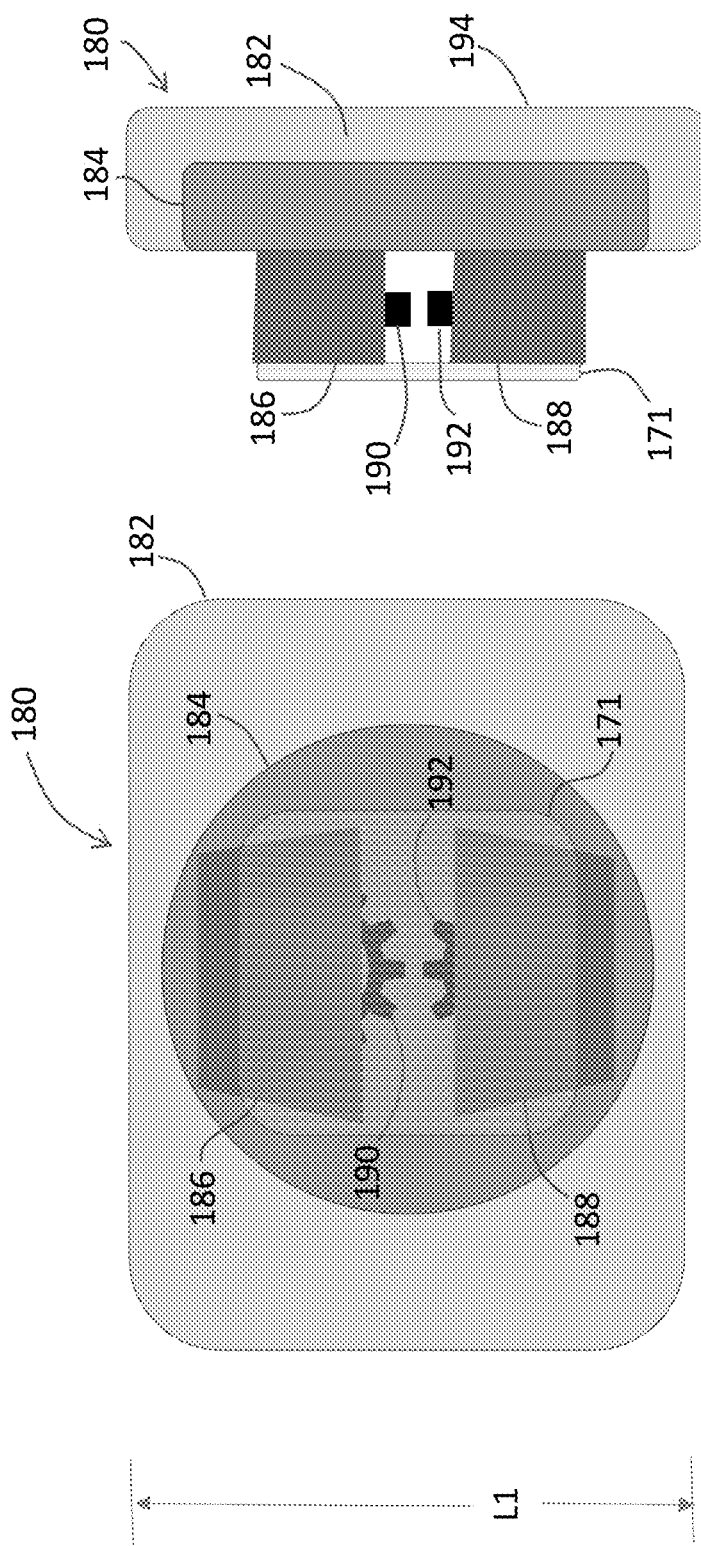

ORTHODONTIC SYSTEMS

CROSS-REFERENCE TO RELATED APPLICATIONS

This application claims priority to U.S. Provisional Patent Application 62/252,760, filed on Nov. 9, 2015. This application is related to U.S. patent application Ser. No. 15/160,275, filed on May 20, 2016; Ser. No. 15/160,234, filed on May 20, 2016; Ser. No. 15/160,291, filed on May 20, 2016; Ser. No. 15/160,277, filed on May 20, 2016; and Ser. No. 15/160,255, filed on May 20, 2016. The contents of the above applications are incorporated by reference in their entirety.

TECHNICAL FIELD

This disclosure relates to orthodontic systems.

BACKGROUND

Orthodontic braces are useful in correcting alignment of teeth to proper positions and orientations in the dental arch and to improve dental health. In some examples, orthodontic braces include metal brackets bonded to the teeth and arch wires that are tied to the brackets by elastic ties. The arch wires are designed to apply forces to the brackets and teeth, causing the teeth to slowly move or rotate in prescribed directions. The arch wires are adjusted, e.g., every three or four weeks during treatment to maintain pressure in order to supply prescribed forces to the teeth. There are many types of dental braces. For example, braces can be self-ligating such that the arch wire clips into the brackets without the need for ligatures. Some dental braces use computer-adjusted wires. These braces use the same principle of force delivery by an external source outside of the bracket (e.g., wire, coils, or elastics). In some examples, a bracket may have a base that is angulated to combine torque, angulation, in and out bend, and offsets for each tooth. This enables an unadjusted arch wire to perform variant alignment functions (i.e., with no further wire bending). In some examples, a series of clear molds may be used to produce teeth alignment. Orthodontic treatments generally last for two to three years.

SUMMARY

In a general aspect, an orthodontic system is provided. The system includes at least one orthodontic bracket configured to be attached to a surface of a tooth. The bracket define an archwire slot, in which an archwire is placed in the archwire slot. The bracket includes a gear system, a motor to drive the gear system, and an integrated circuit to control the motor. A computer server is provided to send instructions to the integrated circuit in the orthodontic bracket. The integrated circuit is configured to control the motor according to the instructions from the computer server to drive the gear system to apply a force to the archwire.

In another general aspect, an orthodontic system is provided. The system includes a first orthodontic bracket configured to be attached to a surface of a first tooth, the first bracket defining a first archwire slot; and a second orthodontic bracket configured to be attached to a surface of a second tooth, the second bracket defining a second archwire slot. A first archwire segment having a first portion and a second portion is provided, in which the first portion passes through the first archwire slot. A second archwire segment having a first portion and a second portion is provided, in which the first portion passes through the second archwire slot. The system includes a gear module coupled to the second portion of the first archwire and the second portion of the second archwire, in which the first bracket, the first archwire segment, the gear module, the second archwire segment, and the second bracket are positioned along an arch. The gear module generates a first force that is applied to the second portion of the first archwire segment and a second force that is applied to the second portion of the second archwire segment. The system includes a motor to drive the gear module, an integrated circuit to control the motor; and a computer server configured to send instructions to the integrated circuit. The integrated circuit is configured to control the motor according to the instructions from the computer server to drive the gear module to apply the first and second forces to the first and second archwire segments.

In another general aspect, an orthodontic treatment method is provided. The method includes attaching at least one orthodontic bracket to a surface of a tooth, in which the bracket defines an archwire slot, and an archwire is placed in the archwire slot. The bracket includes a gear system, a motor to drive the gear system, and an integrated circuit to control the motor. The method includes using a computer server to send instructions to the integrated circuit in the orthodontic bracket, in which the integrated circuit is configured to control the motor according to the instructions from the computer server to cause the motor to drive the gear system to apply a force to the archwire.

In another general aspect, an orthodontic treatment method is provided. The method includes attaching a first orthodontic bracket to a surface of a first tooth, in which the first bracket defines a first archwire slot. The method includes attaching a second orthodontic bracket to a surface of a second tooth, in which the second bracket defines a second archwire slot. The method includes passing a first portion of a first archwire segment through the first archwire slot; passing a first portion of a second archwire segment through the second archwire slot; and positioning the first bracket, the first archwire segment, the gear module, the second archwire segment, and the second bracket along an arch. The method includes sending, from a computer server, instructions to an integrated circuit; using the integrated circuit to control a motor according to the instructions from the computer server; using the motor to drive a gear module; using the gear module to apply a first force to a second portion of the first archwire segment; and using the gear module to apply a second force to a second portion of the second archwire segment.

In another general aspect, a method for orthodontic treatment is provided. The method includes receiving first information associated with a dental treatment plan; based on the first information, generating a first set of instructions; and sending the first set of instructions wirelessly to an orthodontic bracket to cause the orthodontic bracket to apply a first prescribed force to a tooth according to the first set of instructions.

In another general aspect, a computer readable medium storing executable instructions is provided. The executable instructions, when executed by a computer, cause the computer to: receive first information regarding a dental treatment plan; based on the first information, generate a first set of instructions; and send the first set of instructions wirelessly to an orthodontic bracket to cause the orthodontic bracket to apply a first prescribed force to a tooth according to the first set of instructions.

Other aspects include other combinations of the features recited above and other features, expressed as methods, apparatus, systems, program products, and in other ways. Advantages of the aspects and implementations may include one or more of the following. The orthodontic brackets can be active brackets or smart brackets. A remote orthodontic system can allow active brackets or smart brackets to be remotely controlled or adjusted. The active brackets can generate a force, and the force applied to the teeth can be increased or decreased while the patient is at home. The progress of teeth alignment can be monitored remotely. The remote orthodontic system can provide feedback and report symptoms, if any, to the orthodontist. In cases where adjustments to the original treatment plans are needed, the force adjustments can be made and applied while the patient is at home without the need to visit the dental clinic. The system can also provide an estimate of the remaining treatment time based on the current progress of treatment. The system can reduce the trial and error in orthodontic treatment by using proper biomechanical pre-planning and insistent re-adjustment and monitoring. The system can improve the accessibility for orthodontic treatment in rural areas, and may reduce the number of days that school children miss classes. The orthodontic treatment outcomes may be more predictable, leading to a better quality with potentially reduced treatment side effects.

DESCRIPTION OF DRAWINGS

FIG. 12D is a diagram of a base of another exemplary e-Bracket.

FIGS. 13A, 13B, 14A, and 14B are diagrams of exemplary e-Brackets.

FIG. 16 is a diagram of an external front view of an exemplary smart node.

FIGS. 17A to 17D are diagrams of cross sectional views of the exemplary smart node along the longitudinal direction of the orthodontic wire.

FIGS. 20 to 23 are diagrams of tract arch wires.

FIGS. 26A and 26B are diagrams of an exemplary e-Tract bracket.

Like reference symbols in the various drawings indicate like elements.

DETAILED DESCRIPTION

This document describes an orthodontic system that enables an orthodontist to remotely monitor orthodontic braces on patients and make adjustments when necessary in a precise and predictable manner. In some implementations of the remote orthodontic system, the orthodontic system includes smart brackets in which each bracket has a miniature motor that drives a miniature gear, which in turn drives small rods or posts that push against an arch wire, generating a reaction force that pushes against the bracket's wings, in which the reaction force is transferred to the corresponding tooth to provide the required force for alignment of the tooth. The number of miniature motor(s) and the configuration of the motor(s) can vary depending on designs and functions. For example, the orthodontic system can include smart brackets in which each bracket has two miniature motors that drive miniature gears, which in turn pull or push an arch wire to generate opposing forces for alignment of the corresponding tooth (by generating couple forces system). In other implementations of the remote orthodontic system, the orthodontic system includes smart brackets in which each bracket has one or more miniature motors that drive one or more miniature gears, which in turn drive a rotatable base to provide root torque to the bracket for generating a force for alignment of the corresponding tooth. In some implementations of the remote orthodontic system, the orthodontic braces include arch wire segments connected by smart brackets in which each bracket has one or more miniature motors that apply forces to the arch wire segments, such that the combination of the forces generated by the plurality of brackets provide the proper amount of force for the alignment of each individual tooth.

Figure 1:
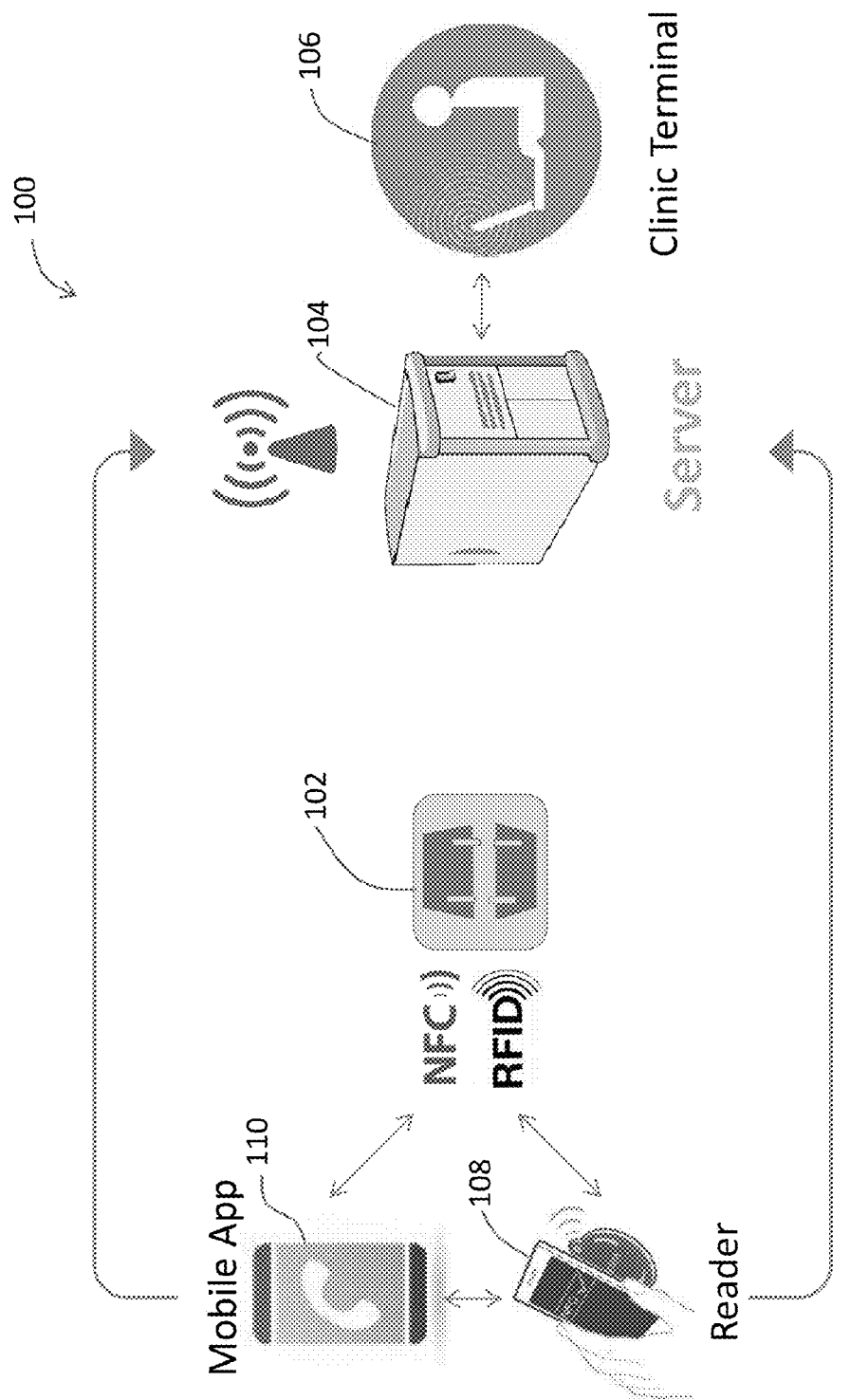
FIG. 1 is a diagram of an exemplary remote orthodontic system.

Referring to FIG. 1, a remote orthodontic system 100 includes orthodontic braces composed of smart brackets 102 (only one is shown in the figure) that communicate wirelessly with a computer server 104. The computer server 104 can be a physical machine located at the patient's home, or it can be a virtual server commonly referred to as a cloud server that resides remotely. The following describes examples in which the computer server 104 is a cloud server. In some examples, the computer server 104 may interact wirelessly with the brackets 102 by receiving signals from or sending signals to the brackets 102. This interaction occurs through, e.g., a home-based reader 108 or a user's cell phone 110, while the computer server 104 communicates with a clinic terminal 106 at a dental clinic. The computer server 104 receives signals from the brackets 102 (e.g., through the reader 108 or the cell phone 110), determines the current configurations of the brackets 102, determines whether adjustments are necessary, and sends back signals using the same route (e.g., through the reader 108 or the cell phone 110) to the brackets 102 in order to control motors in the brackets 102 to make the necessary adjustments. The computer server 104 communicates with the terminal 106 at the dental clinic to enable an orthodontist and/or other healthcare providers to monitor the configurations of the brackets 102 and enter commands to make additional adjustments when necessary.

In some implementations, when the patient first visits the orthodontist, the orthodontist may prescribe a treatment plan that specifies the amount and direction of force to be applied to each tooth at each of different time periods. The orthodontist may provide an electronic file that includes the treatment plan, and the patient may download, from the computer server 104, the electronic file having updated data containing the treatment plan to the reader 108 or the cell phone 110. The reader 108 or the cell phone 100 may execute an orthodontic application program that uses the information about the treatment plan to interact with the brackets 102.

After the first visit to the orthodontist, and at each follow up visit every three or four weeks, the orthodontist executes the orthodontic treatment program on the server 104. The orthodontic treatment program may analyze signals received from the brackets 102 to determine the progress of teeth alignment. The program may compare the current progress with the prescribed treatment plan and determine which brackets need to be adjusted to increase or decrease the force applied and its direction to the corresponding tooth, or to adjust the torque applied by the bracket to the tooth. The program instructs the server 104 to send signals to the brackets 102 to configure the brackets 102 such that each tooth receives the proper amount of force metrics according to the prescribed treatment plan.

Because the adjustments to the brackets 102 can be conveniently performed at the patient's home, the treatment plan may have instructions for more frequent bracket adjustments at finer time intervals, such as twice every month. The patient has the option of making adjustments to the brackets at times that are convenient to the patient.

The wireless reader 108 can interact wirelessly with the brackets 102 using a communication protocol similar to, e.g., the RFID protocol, Bluetooth protocol, or other protocols. The wireless reader 108 may be connected to the computer server 104 through a wire connection or a wireless link. The mobile phone 110 executing the orthodontic application program may interact wirelessly with the brackets 102 using a communication protocol similar to, e.g., the near-field communication protocol, Bluetooth protocol, or other protocols. The system may operate in, e.g., the 401-406 MHz, 902-928 MHz, 2400-2483.5 MHz, and/or 5725-5850 MHz bands. The mobile phone 110 may communicate with the computer server 104 through a wireless link.

In some implementations, the smart bracket 102 has sensors that can detect the amount of force (and/or the position trajectories) being applied to the tooth through the arch wire. Alternatively the sensors can be attached to or embedded in the arch wire itself. The sensors provide feedback signals so that the orthodontic treatment program executing on the computer server 104 can determine that the correct amount of force and the direction of force are applied to each tooth to ensure its proper alignment and positioning. If, after configuring the brackets 102, the sensors determine that the force/direction applied to the tooth deviates from the prescribed amount by more than a threshold value, the program may generate an alert signal, indicating that the patient should contact the orthodontist. Alternatively, the program can readjust and apply the new biomechanical force specifications. Upon receiving an instruction from the patient, the computer server 104 may send the data from the sensor to the clinic terminal 106 so that the orthodontist may determine whether it is possible to reconfigure the brackets remotely, or to inform the patient that it is necessary to return to the dental clinic for further examination and adjustment.

Figure 2:
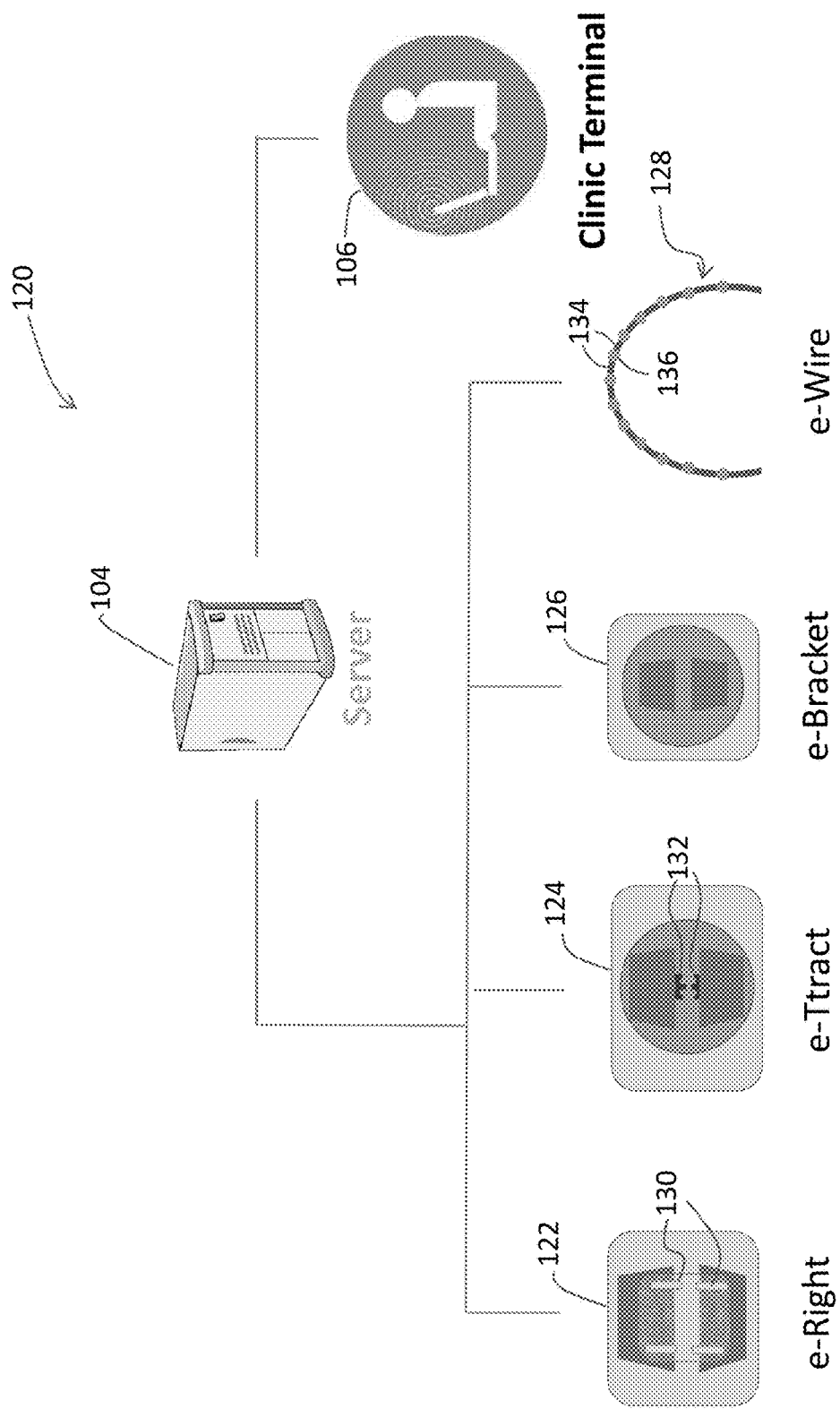
FIG. 2 is a diagram of various modules of the remote orthodontic system.

Referring to FIG. 2, a remote orthodontics system 120 may include a server 104 that communicates with different types of smart orthodontic braces, or orthodontic braces that include more than one type of smart brackets (individually or as a group). The computer server 104 may execute an orthodontic treatment program that is configured to control the various types of braces having various types of smart brackets. The server 104 may communicate with a clinic terminal 106 to enable an orthodontist to remotely monitor treatment progress or provide adjustments.

For example, one type of smart bracket is bracket 122, referred to as the e-Right bracket. The e-Right bracket 122 includes miniature motors that drive miniature gears, which in turn drive small rods that push against an arch wire inserted into a slot of a bracket attached to a tooth. The small rods provide forces that in combination produce the desired amount of force in the desired direction that is applied to the corresponding tooth to provide the required movement for alignment of the tooth.

A second type of smart bracket is bracket 124, referred to as the e-Tract bracket. The e-Tract bracket has two miniature motors that drive miniature gears 132, which in turn pull or push an arch wire (inserted in between the gears) to generate retracting or protracting forces for movement and/or alignment of the corresponding tooth (or a group of teeth).

A third type of smart bracket is bracket 126, referred to as the e-Bracket in this document. The e-Bracket has one or more miniature motors that drive one or more miniature gears, which in turn drive a rotatable base to provide a torque to the bracket 126 for generating a force for alignment of the corresponding tooth.

A fourth type of orthodontic braces variation is e-Wire braces 128. The e-Wire braces 128 include arch wire segments 134 connected to smart brackets 136 in which each bracket 136 has one or more miniature motors that apply forces to the arch wire segments 134, such that the interaction of the brackets 136 and wire segments 134 result in the proper amount of forces being applied to the teeth that need adjustment. Each arch wire segment is attached to the corresponding tooth surface in order to translate the delivered force. A patient may use any configuration of two or more of the e-Right bracket 122, e-Tract bracket 124, e-Bracket 126, or e-Wire braces 128 at the same time.

Figure 3:
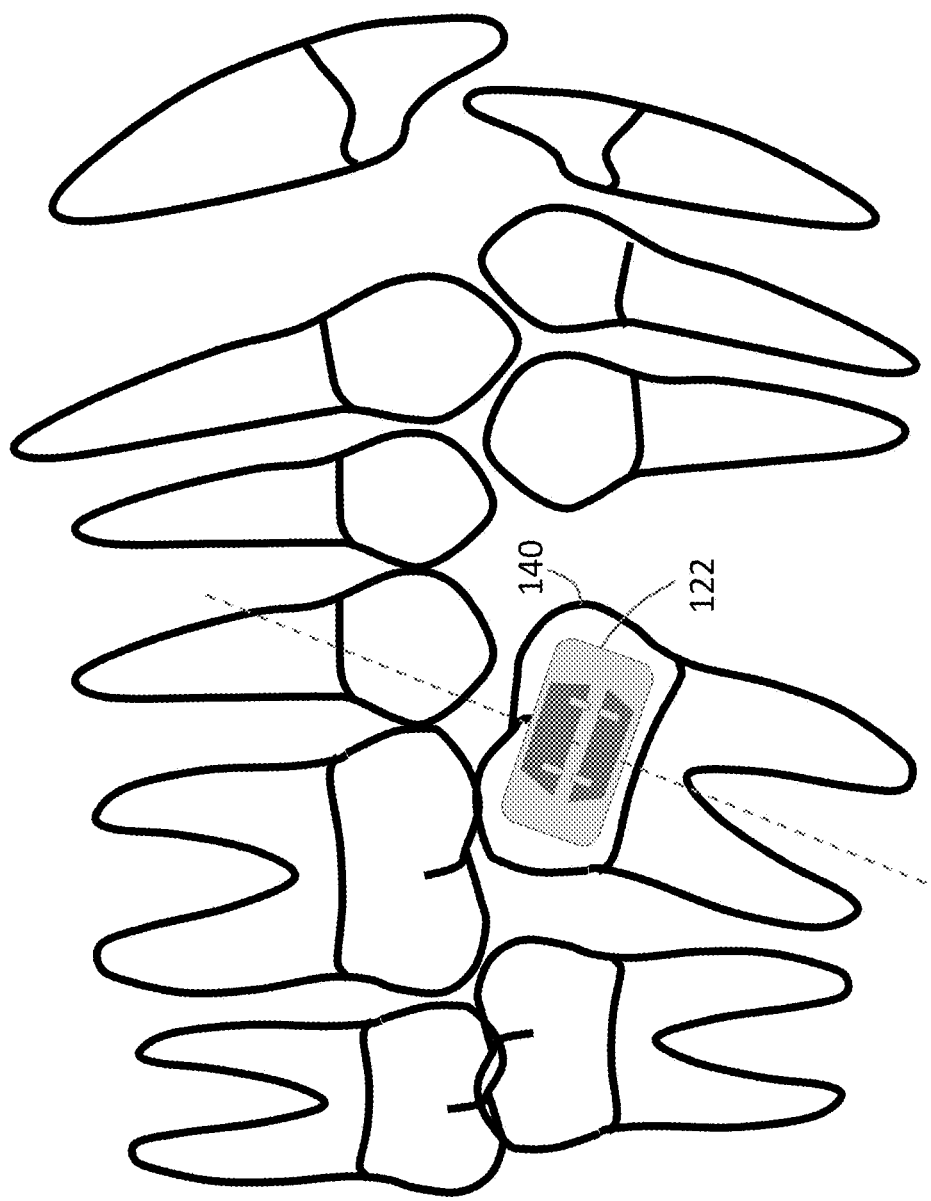
FIG. 3 is a diagram of an e-Right bracket attached to a tooth.

Referring to FIG. 3, an e-Right bracket 122 may be attached to a tooth 140 (in this example, a molar tooth) and provide a force for moving the tooth. This is useful for up-righting a misaligned tooth (e.g., mesially tilted tooth).

Figure 4:
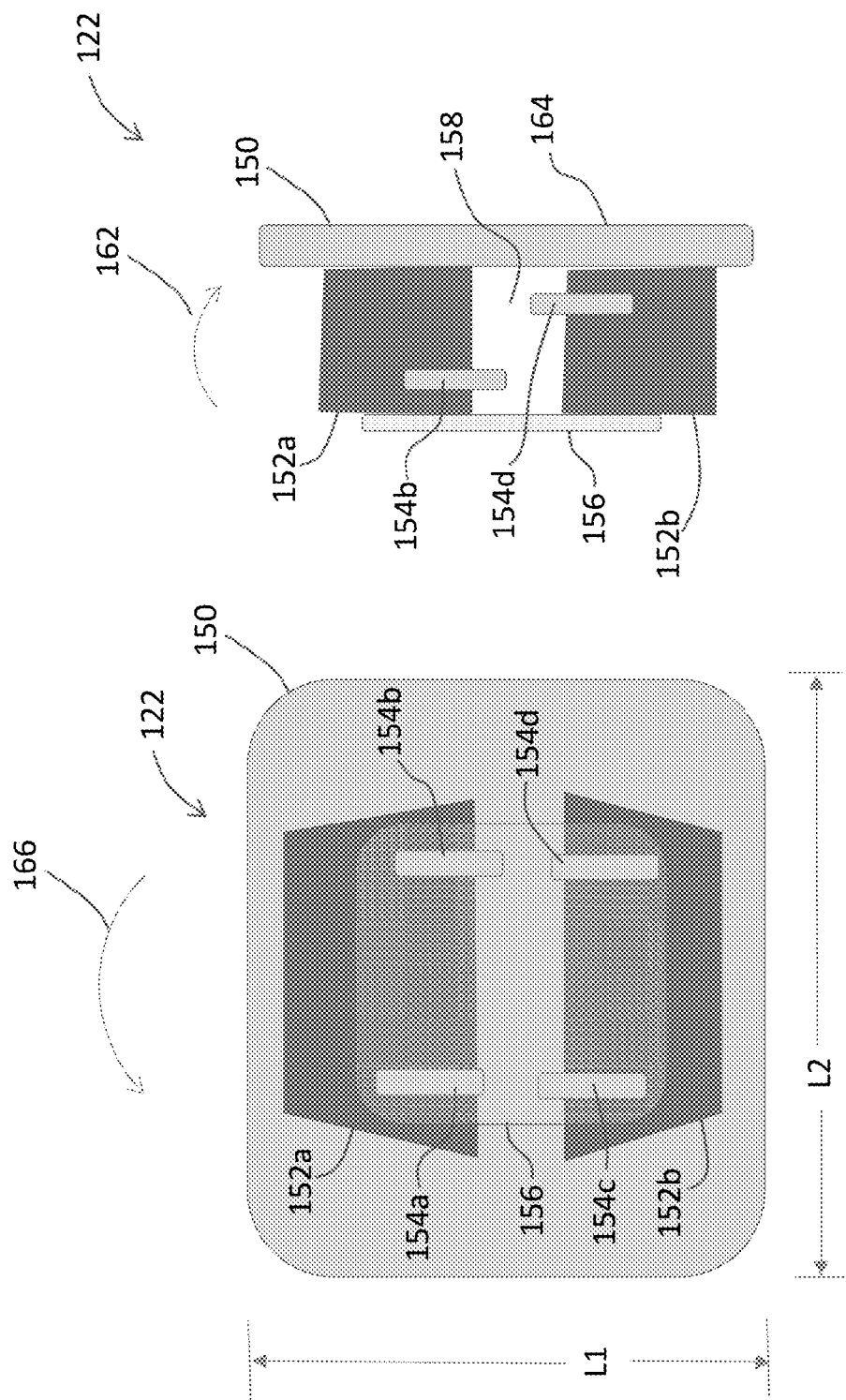
FIGS. 4A, 4B, 5A, and 5B are diagrams of exemplary e-Right brackets.

FIG. 4A is a front view of the e-Right bracket 122, and FIG. 4B is a side view of the e-Right bracket 122. The e-Right bracket 122 includes a base 150, an upper support 152a, a lower support 152b, and a cover 156. A serrated surface 164 of the base 150 attaches to a tooth that is subject to treatment. The upper support 152a and lower support 152b are connected to the base 150. The upper support 152a provides support for upper rods 154a and 154b that may protrude from the upper support 152a into a space 158 between the upper support 152a and the lower support 152b. The lower support 152b provides support for lower rods 154c and 154d that may protrude from the lower support 152b into the space 158. The cover 156 enables arch wire engagement within the space 158 so the operations of the rods 154a to 154d can have effect on the arch wire and eventually produce tooth movement.

An orthodontic arch wire 160 (see FIGS. 5A and 5B) passes through the space 158 between the upper rods 154a, 154*b* and the lower rods 154*c*, 154*d*. The orthodontic arch wire 160 conforms to the dental arch and passes through various brackets attached to the teeth whose alignment need adjustment or to serve as anchor points. The cover 156 can be either fixed or removable, and is used to ligate the arch wire 160 with the bracket slot. As the upper rods 154*a*, 154*b* and lower rods 154*c*, 154*d* push against the arch wire 160, the reaction forces (couple force system) pushing back against the rods generate a force and/or torque that is applied to the bracket 122. Since the bracket 122 is securely attached to the tooth, the force and/or torque is transferred to the tooth, providing the necessary forces for alignment of the tooth.

In some implementations, the rods 154*a* and 154*b* are driven by a first miniature gear in counter directions such that if the rod 154*a* is driven upwards, then the rod 154*b* is also driven downwards. Alternatively, if the rod 154*a* is driven downwards, then the rod 154*b* is driven upwards. Similarly, the rods 154*c* and 154*d* are driven by a second miniature gear in counter directions such that if the rod 154*c* is driven upwards, then the rod 154*d* is also driven downwards. Alternatively, if the rod 154*c* is driven downwards, then the rod 154*d* is driven upwards.

Figure 5:
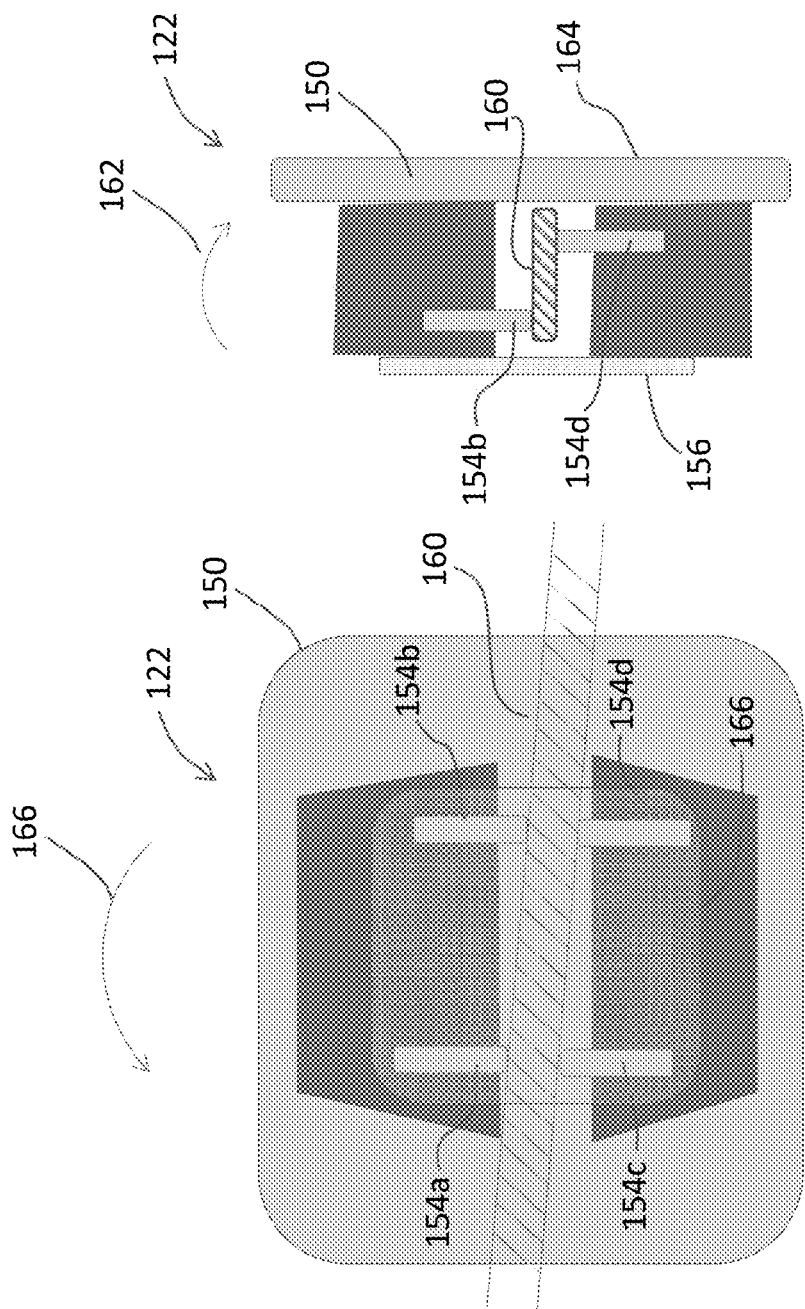

In the example shown in FIGS. 4A and 5A, the upper rod 154*b* is lower than the upper rod 154*a*, and the lower rod 154*d* is lower than the lower rod 154*c*. This causes the arch wire 160 to push against the upper rod 154*b* and the lower rod 154*c*, generating a counterclockwise rotation 166 on the bracket 122 about an axis perpendicular to the plane of the base 150 (when viewed from a direction facing the bracket 122).

Similarly, when the upper rod 154*b* is higher than the upper rod 154*a*, and the lower rod 154*d* is higher than the lower rod 154*c*, the arch wire 160 pushes against the upper rod 154*b* and the lower rod 154*c*, generating a clockwise torque 166 on the bracket 122 about an axis perpendicular to the plane of the base 150 (when viewed from a direction facing the bracket 122).

In some implementations, as shown in FIG. 4B, the upper rods 154*a* and 154*b* are substantially aligned along a first plane parallel to a surface of the base 150, i.e., the distance between the rod 154*a* to the base 150 is substantially the same as the distance between the rod 154*b* to the base 150. The lower rods 154*c* and 154*d* are substantially aligned along a second plane parallel to the surface of the base 150, i.e., the distance between the rod 154*c* to the base 150 is substantially the same as the distance between the rod 154*d* to the base 150. The first plane can be offset relative to the second plane, such that the distance between the upper rods 154*a*, 154*b* to the base 150 is different from the distance between the lower rods 154*c*, 154*d* to the base 150.

In the example shown in FIGS. 4B and 5B, the upper rod 154*b* is farther from the base 150 than the lower rod 154*d*. This causes the arch wire 160 to push against the upper rod 154*b* and the lower rod 154*d*, generating a clockwise rotational torque 162 on the bracket 122 about an axis parallel to the plane of the base 150 (when viewed along a direction facing a right side of the bracket 122). Similarly, the interaction between the upper rod 154*a*, lower rod 154*c*, and the arch wire 160 will cause the arch wire 160 to push against the upper rod 154*a* and the lower rod 154*c*, generating a clockwise torque on the bracket 122 (when viewed along a direction facing a right side of the bracket 122).

The first torque derived from the interaction of the arch wire 160 and the rods 154*b*, 154*d* can be different from the second torque derived from the interaction of the arch wire 160 and the rods 154*a*, 154*c*. For example, if the rods 154*b*, 154*d* push against the arch wire 160 with greater force, as compared to the rods 154*a*, 154*c*, then the first torque will be greater than the second torque. This provides the orthodontist greater flexibility in designing the proper force system applied to the tooth for alignment. For example, it is possible to set one gear (see FIG. 6) and corresponding rods to provide the required force, and use the opposing gear and corresponding rods to function as a stopper. Initially, the rods are set to provide some space for movement of the arch wire 160. The gear and corresponding rods provide the required force to move the arch wire 160 along a prescribed path resulting in correcting the alignment of the tooth. The opposing gear and corresponding rods stop the movement of the arch wire 160 at a prescribed end position.

In some examples, the vertical dimension (L1) of the bracket 122 is about 5 mm, the horizontal dimension (L2) of the bracket 122 is about 11 mm, and the thickness of the bracket 122 at its thickest portion is about 4 mm. The dimensions of the bracket 122 can vary depending on the size of the tooth being treated and the amount of force required. For example, the bracket for treating a molar tooth can be larger than a bracket for treating a canine tooth. A larger bracket may house a more powerful motor that can provide a greater force than that provided by a smaller bracket. The force exerted by the bracket 122 on the tooth can be, e.g., about 1 to 2 Newtons.

Figure 6:
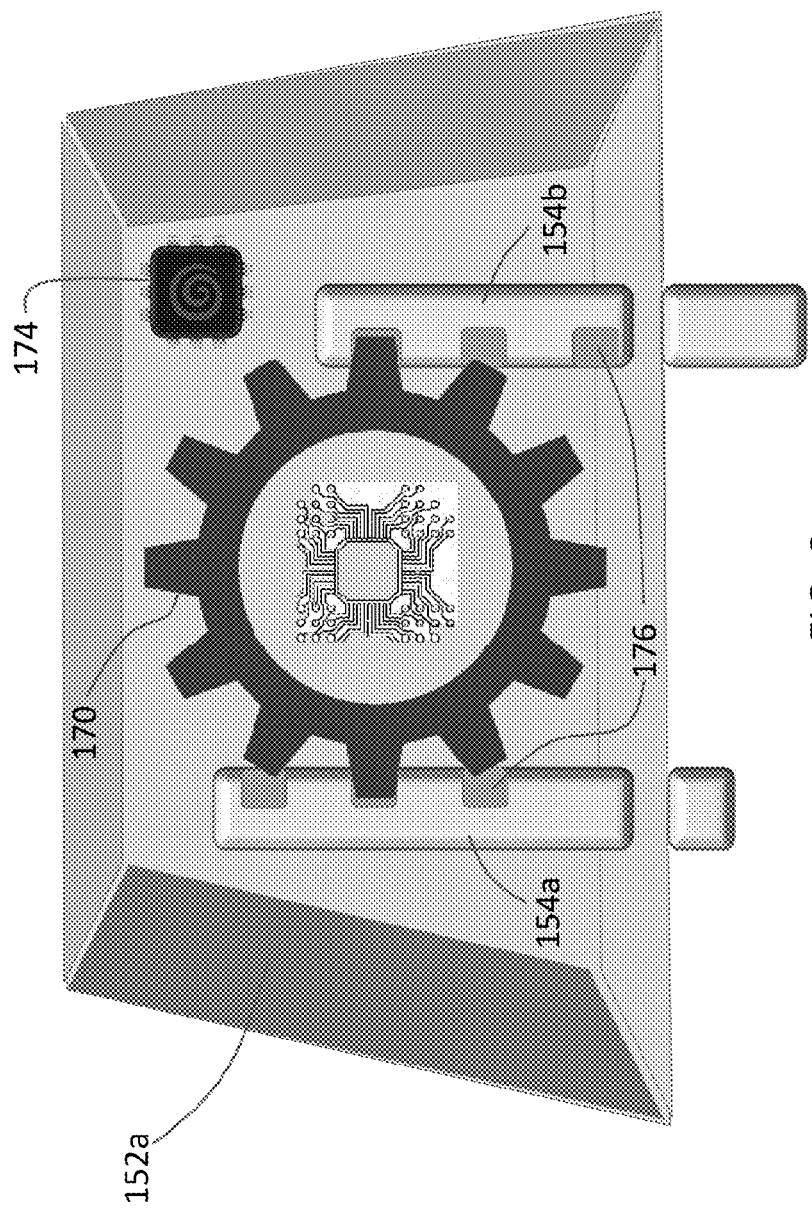
FIG. 6 is a diagram of an upper support module of the e-Right bracket.

Referring to FIG. 6, the upper support 152*a* supports a miniature gear 170 for driving the rods 154*a*, 154*b* up or down. The gear 170 is driven by a miniature motor (not shown in the figure). For example, the miniature gear 170 and miniature motor can be fabricated using micro electromechanical systems (MEMS) technology. The gear 170 engages notches 176 formed in the rods 154*a*, 154*b*. When the gear 170 rotates in a clockwise direction (when viewed from a direction facing the front side of the bracket 122), the gear 170 pushes the rod 154*b* downwards and pushes the rod 154*a* upwards. Conversely, when the gear 170 rotates in a counterclockwise direction, the gear 170 pushes the rod 154*b* upwards and pushes the rod 154*a* downwards.

An integrated circuit chip 174 includes circuitry for communicating with the computer server 104, the reader 108, and/or the mobile device 110. The chip 174 also includes circuitry for controlling the operation of the motor.

The upper support 152*a* provides a sealed environment for the motor, gear 170, and chip 174. The rods 154*a*, 154*b* protrude from the upper support 152*a* through small openings. The openings are made with precision and provided with insulating rubber linings to prevent liquids from entering the bracket. The gaps between the rods 154*a*, 154*b* and the edges of the openings are very small such that saliva or food particles do not enter through the gaps. In some implementations, an insulating rubber lining can be provided at the gap to further prevent liquids from entering the bracket. The electrical contacts of the chip 174 and the motor can be sealed with, e.g., epoxy so that even if some fluid were to enter through the gaps, it would not affect the operation of the chip 174 and the motor.

The lower support 152*b* has a configuration similar to the upper support 152*a*. The lower support 152*b* also has a miniature motor and a miniature gear for driving the rods 154*c*, 154*d*. A chip controls the operations of the motor and gear. In some implementations, a single chip controls the operations of the motors in the upper support 152*a* and the lower support 152*b*. For example, the chip in the upper support 152*a* may send signals to the motor in the lower support 152*b* through signal lines that extend from the upper support 152*a* through the base 150 to the lower support 152*b*. The chip can also be placed in the base 150, in which the signal lines extend from the base to the upper and lower supports 152*a*, 152*b*.

The upper and lower gears can work in combination. For example, both the lower and upper gears can rotate in a clockwise direction, such that upper rod 154*b* exerts a downward force, the lower rod 154*c* exerts an upward force, resulting in a couple force system leading to a counter-clockwise rotation of the attached tooth around its center of rotation. In the example of FIG. 3, in which the tooth 140 is in the lower right quadrant, the counter-clockwise rotation results in distal (backward) tipping that corrects the initial mesial (forward) tipping.

Figure 7:
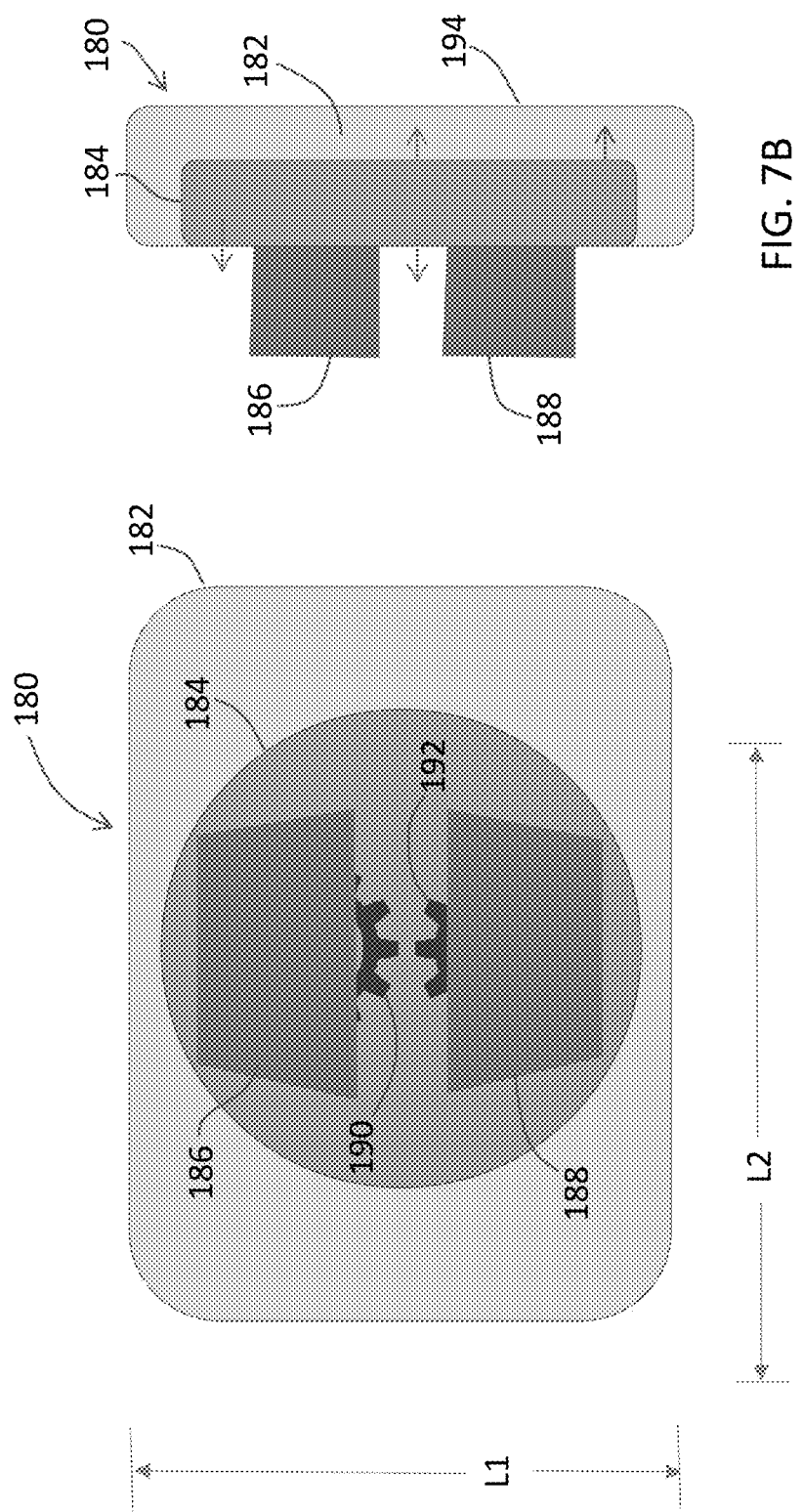
FIGS. 7A and 7B are diagrams of an exemplary e-Tract bracket.

Referring to FIGS. 7A and 7B, in some implementations, an e-Tract bracket 180 can be used as an auxiliary tool with the existing orthodontic bracket system, or in combination with new brackets (such as the e-Bracket described below). The e-Tract bracket 180 can generate retraction or protraction forces through simultaneous rotating gear action coupled with an inter-locking serrated arch wire. The type of traction would depend on the gears' rotation direction. The e-Tract bracket 180 can be used in combination with other brackets to provide a bracing function to facilitate the overall alignment. FIG. 7A shows a front view of the bracket 180 while FIG. 7B shows a side view of the bracket 180. Gears on the bracket 180 can lock onto notches on a specially designed arch wire to generate a retraction or protraction force on the arch wire. The e-Tract bracket 180 can have, e.g., a height L1 of about 5 mm and a length L2 of about 11 mm. The dimensions of the e-Tract bracket 180 can vary depending on the amount of force required and the size of the tooth on which the bracket 180 is attached.

The bracket 180 includes a base 182, a support 184, an upper member 186, and a lower member 188. In some examples, a back surface 194 of the base 182 attaches to a molar (last) tooth. In some examples, the base 182 is fitted on a mini-screw supporting implant. The upper member 186 houses a miniature motor and a miniature gear 190. The miniature motor in the upper member 186 drives the miniature gear 190. The lower member 188 houses a miniature motor and a miniature gear 192. The miniature motor in the lower member 188 drives the miniature gear 192.

Figure 8:
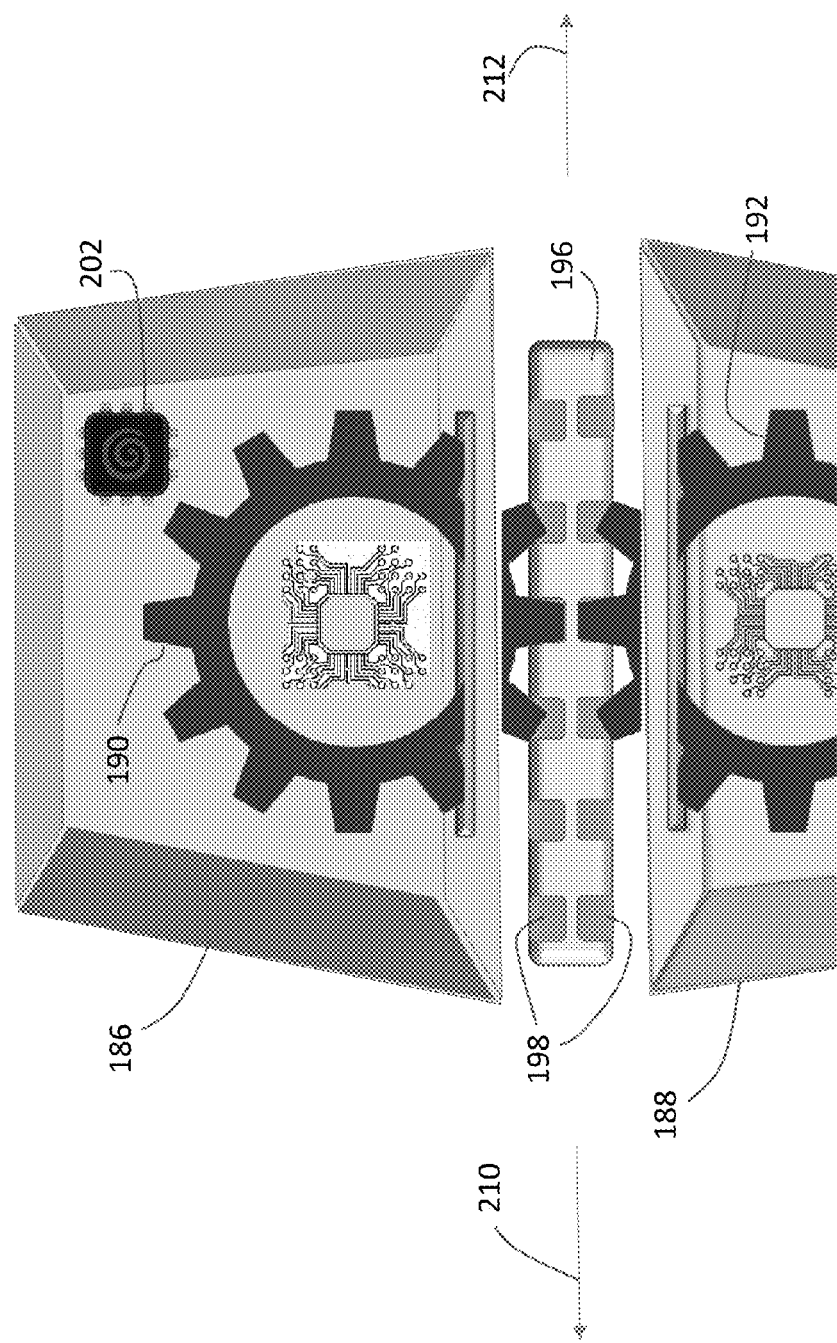
FIG. 8 is a diagram of the e-Tract bracket with an arch wire.

Referring to FIG. 8, when the upper gear 190 rotates in a clockwise direction and the lower gear 192 rotates in a counterclockwise direction, the teeth of the gears 190, 192 engage notches 198 in the arch wire 196 and pulls the arch wire 196 in a direction 210 towards the left (when viewed from a direction facing the front side of the bracket 180). Conversely, when the upper gear 190 rotates in a counter-clockwise direction and the lower gear 192 rotates in a clockwise direction, the teeth of the gears 190, 192 engage the notches 198 in the arch wire 196 and pulls the arch wire 196 in a direction 212 towards the right. The arch wire 196 can be coupled to other brackets so that the pulling (or pushing) force generated by the gears 190, 192 can be used to generate a force that is applied to the other brackets and the teeth to which the brackets are attached. The upper member 186 includes an integrated circuit chip 202 that has circuitry for controlling the miniature motor in the upper member 186. The lower member 188 also includes an integrated circuit chip that has circuitry for controlling the miniature motor in the lower member 188. In some implementations, a single chip controls the operations of the motors in the upper and lower members 186, 188. The chip can also be placed in the base 182. The integrated circuit chip 202 in the upper member 186 and the integrated circuit chip 202 in the lower member 188 can communicate wirelessly to external devices, such as the reader 108 or the cell phone 110.

Referring to FIGS. 26A and 26B, in some implementations, the e-Tract bracket 180 (FIG. 7A) can have a fixed or removable cover 171 that is used to ligate the arch wire 196 (FIG. 8) with the bracket slot.

In some implementations, the gears 190 and 192 can be driven manually. For example, a first miniature screw can be provided in the upper member 186, in which the thread of the screw engages the gear 190. The head of the first miniature screw can protrude outside of the upper member 186 so that the dentist or the patient can turn the first miniature screw to rotate the gear 190. Similarly, a second miniature screw can be provided in the lower member 188, in which the thread of the screw engages the gear 192. The head of the second miniature screw can protrude outside of the lower member 188 so that the dentist or the patient can turn the second miniature screw to rotate the gear 192. As the gear 190 and/or 192 are rotated, the arch wire 196 is pushed or pulled accordingly. In some implementations, the upper gear 190 can be manually driven, where the lower gear 192 simultaneously follows the action of the upper gear 190. Alternatively, the gear 190 can be joined with the gear 192 via, e.g., a cord, through the bracket support structure 184, to allow for a simultaneous coupled gear action. Additionally, the gear 190 (and/or 192), has a locking mechanism to prevent counter rotation after activation on a certain direction.

Figures 9A, 9B:
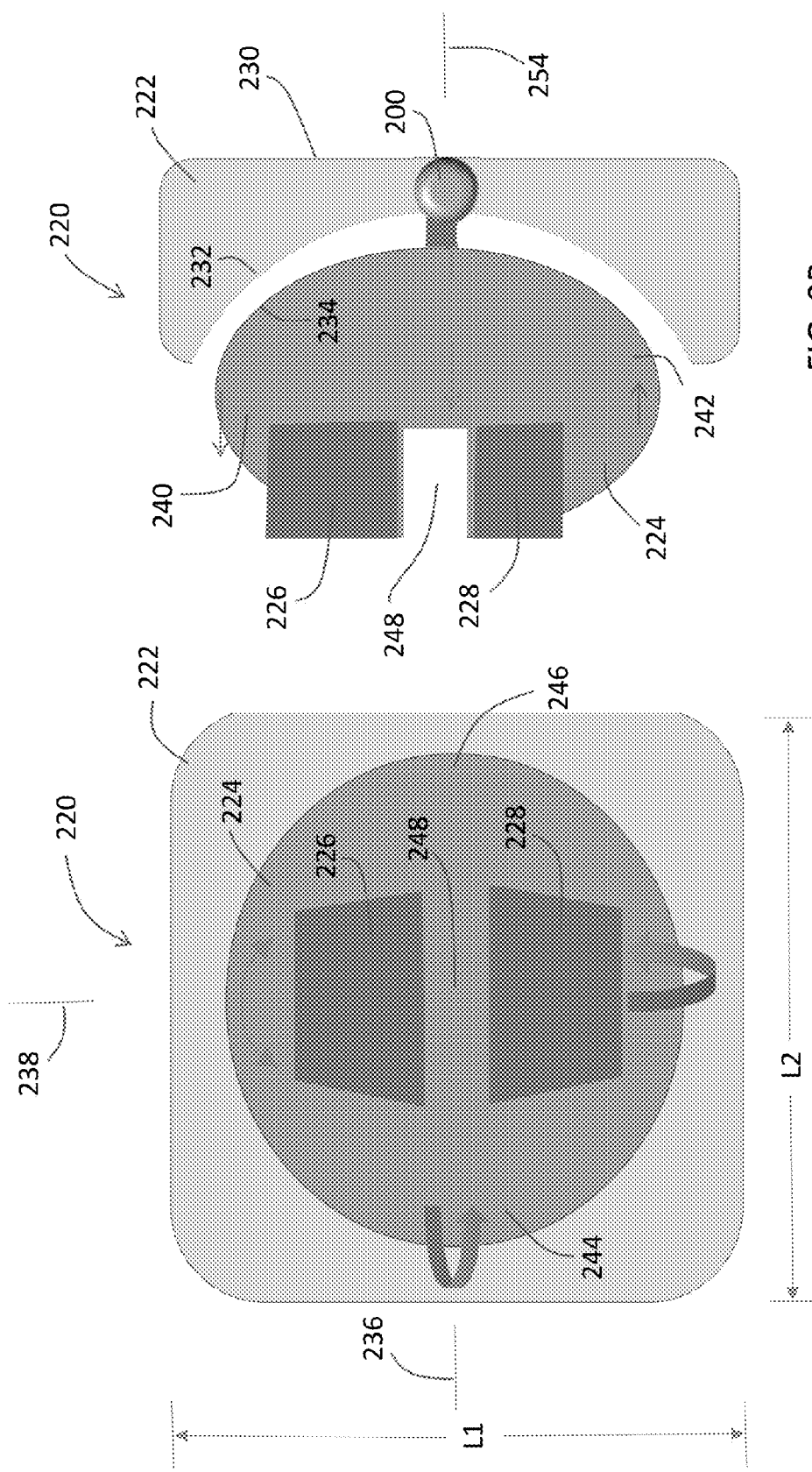
FIGS. 9A and 9B are diagrams of an exemplary e-Bracket.

FIG. 9A shows a front view of an orthodontic bracket, referred to as an e-Bracket 220, and FIG. 9B shows a vertical mid-cross sectional view of the e-Bracket 220. The e-Bracket 220 is able to provide tooth alignment in all three-dimensions via a revolving base. The e-Bracket 220 includes a base 222 having a back surface 230 that is configured to be attached to a tooth, and a pivotable module 224 that can pivot relative to the base 222. The base 222 includes a front concave surface 232 that receives a back convex surface 234 of the pivotable module 224.

In some implementations, miniature motors and gear assemblies are configured to push an upper portion 240 of the pivotable module 224 forward or backward, and to push a lower portion 242 of the pivotable module 224 backward or forward, to cause the pivotable module 224 to pivot or rotate about a horizontal axis 236. This provides a torque that can be used for root movement.

Similarly, the miniature motors and gear assemblies are configured to push a left portion 244 of the pivotable module 224 forward or backward, and to push a right portion 246 of the pivotable module 224 backward or forward, to cause the pivotable module 224 to pivot or rotate about a vertical axis 238. This provides a force for correction of tooth alignment (in or out rotation movement).

In some implementations, the miniature motors and gear assemblies are configured to rotate the pivotable module 224 about an axis 254 in a clockwise or counterclockwise direction (as viewed from the front side). In this example, the axis 254 is along a horizontal lingual-facial direction. This provides a force to enable the action of tilting movement (also known as second order bend action).

In some examples, the e-Bracket 220 has a height L1 of about 6 mm and a length L2 of about 5 mm. The e-Bracket 220 can also have a square shape, with a side length of about 5 mm or 6 mm. The dimensions of the e-Bracket can vary depending on the size of the tooth being treated and the amount of force required.

Figure 10:
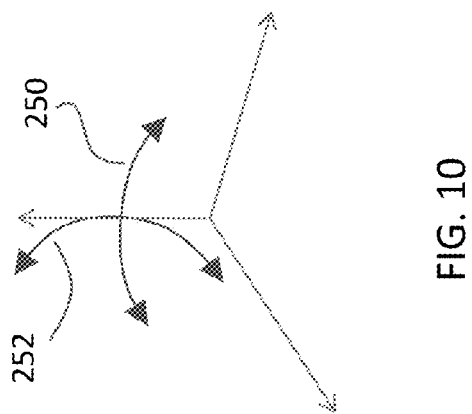
FIG. 10 is a diagram of movement directions of the e-Bracket.

Referring to FIG. 10, by operating the miniature motors and gear assemblies to push the left and/or right portions of the pivotable module 224, the pivotable module 224 can pivot or rotate about the vertical axis, as shown by the bi-directional arrow 250. By operating the miniature motors and gear assemblies to push the upper and/or lower portions of the pivotable module 224, the pivotable module 224 can pivot or rotate about the horizontal axis, as shown by the bi-directional arrow 252. This results in a multi-directional (three dimensional) integrated alignment system.

Figure 11:
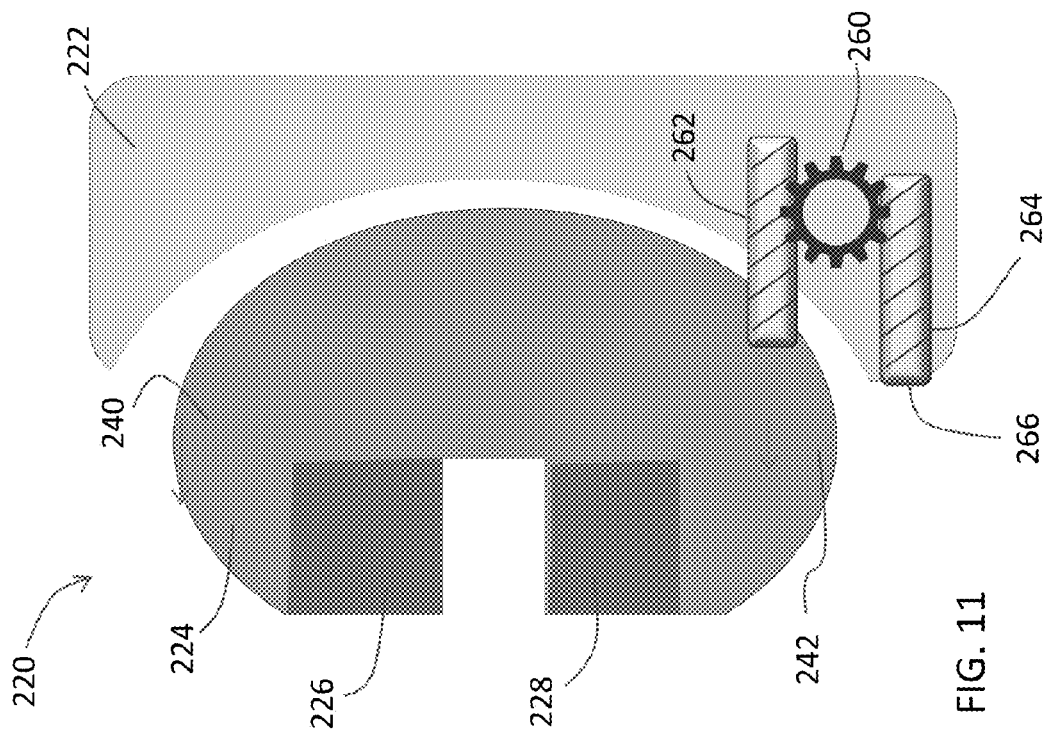
FIG. 11 is a vertical cross sectional view of the e-Bracket along a direction orthogonal to the longitudinal direction of the orthodontic wire.

Referring to FIG. 11, the bracket 220 includes a miniature gear 260 that is supported by the base 222. The gear 260 engages notches in a rod 262 to drive the rod 262 forward or backward. The forward end of the rod 262 is coupled to the lower portion 242 of the pivotable module 224. When the rod 262 moves forward or backward, the rod 262 pushes the lower portion 242 forward or backward, respectively. Thus, by controlling the gear 260, the lower portion 242 can be moved forward or backward. In a similar manner, another gear (not shown in the figure) located at the upper portion of the base 222 drives a rod that in turn pushes the upper portion 240 of the pivotable module 224 forward or backward. Together these gears can cause the pivotable module 224 to pivot or rotate about the horizontal axis 236. The left portion 244 and the right portion 246 of the pivotable module 222 can be moved in a similar manner by two other gears and rods to cause the pivotable module 222 to pivot or rotate about the vertical axis 238.

In some implementations, bevel gears can be used to change the direction of rotation. For example, a miniature motor may drive a first conically shaped bevel gear that rotates about an axis that is parallel to the axis 254 (FIG. 9B), in which the first bevel gear drives a second conically shaped bevel gear that rotates about an axis parallel to the horizontal axis. The second bevel gear shares a same shaft as the gear 260. This allows the motor having an axis parallel to the axis 254 to be able to generate a force that drives the rod 262 forward or backward.

In some implementations, the gear 260 may be driven manually. For example, a lower rod 264 may have one end 266 that extends to outside of the base 222, in which the end 266 has one or more slots that can be driven by a small screwdriver. The rotation of the lower rod 264 drives the gear 260, which drives the upper rod 262 that in turn moves the lower portion 242 of the pivotable module 224.

In some implementations, the pivotable module 224 is connected to a node or ball 200 that fits in a track in the base 222. As the motor and gear assemblies push the upper, lower, left, and/or right portions of the pivotable module 224, the ball 200 moves inside the track while also anchoring the pivotable module 224.

Figure 12A:
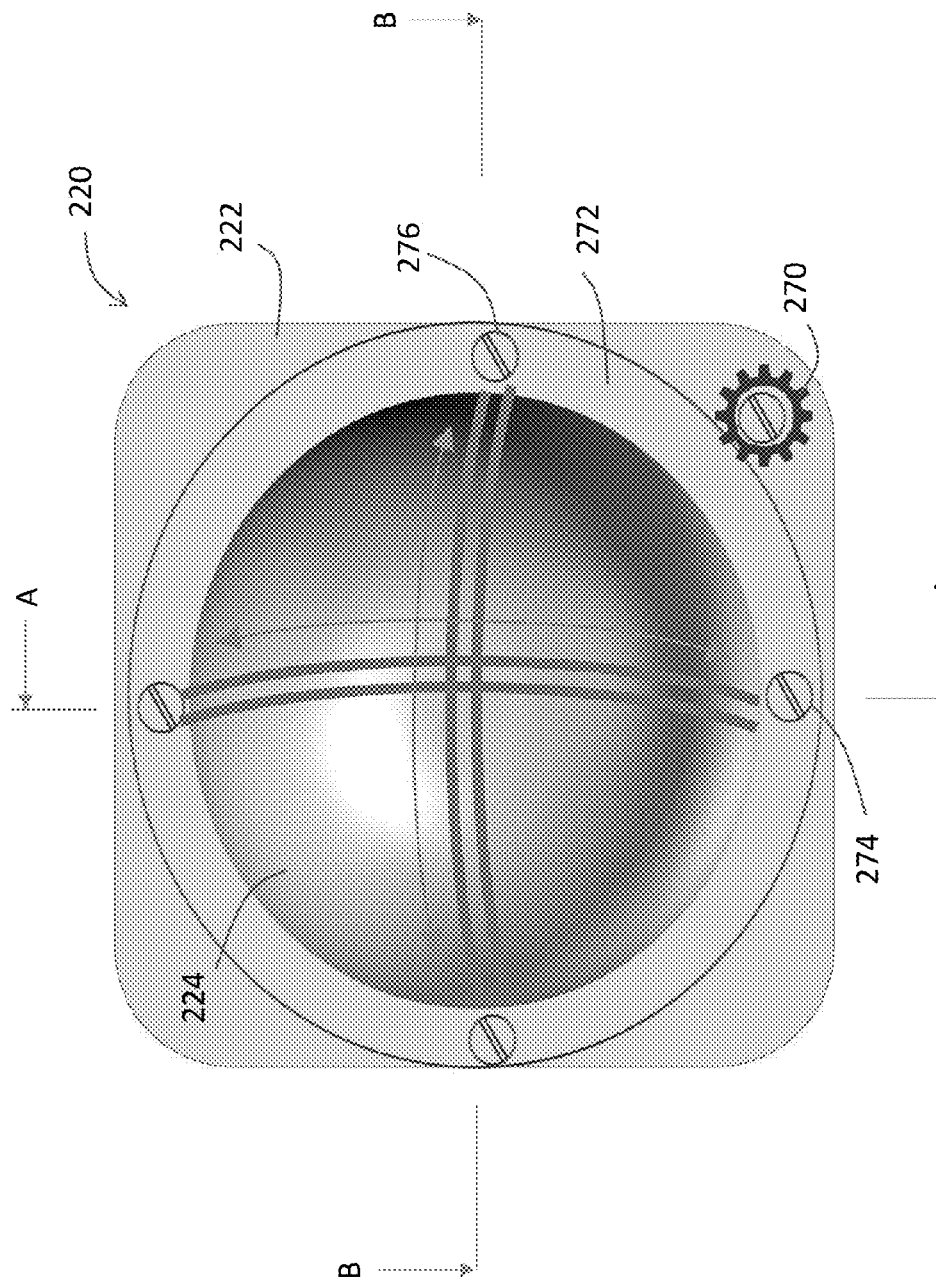
FIG. 12A is a diagram of an exemplary e-Bracket.

Referring to FIG. 12A, a fifth gear 270 can be configured to rotate the pivotable module 224 in a clockwise or counterclockwise direction (when viewed from a direction facing the front side of the bracket 220). The gear 270 can be configured to drive notches made in a circumference of the pivotable module 224, or to drive notches made in a flange 272 attached to the pivotable module 224.

In some implementations, screws 274 and 276 are provided for manually driving the gears of the orthodontic bracket 220. FIG. 12B shows a cross-sectional view of the orthodontic bracket 220 in the direction of the arrows on the line A-A of FIG. 12A. FIG. 12B is similar to FIG. 11 except that the screw 274 has been added. The lower rod 264 has an end that extends to outside of the base 222 and is coupled to the screw 274. When the user turns the screw 274, the lower rod 264 is rotated, which drives the gear 260, which drives the upper rod 262 that in turn moves the lower portion 242 of the pivotable module 224. This allows the pivotable module 224 to rotate about the horizontal axis 236.

Figure 12C:
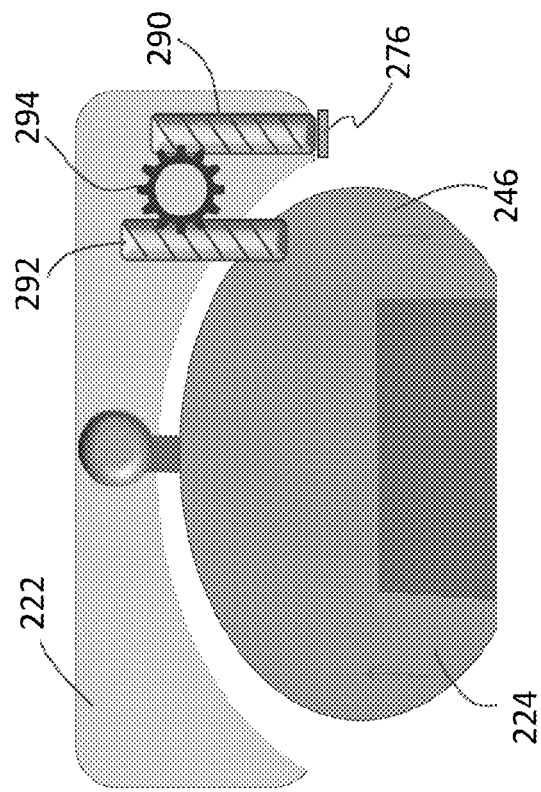
FIGS. 12B and 12C are cross-sectional diagrams of the e-Bracket of FIG. 12A.
Figure 12B:
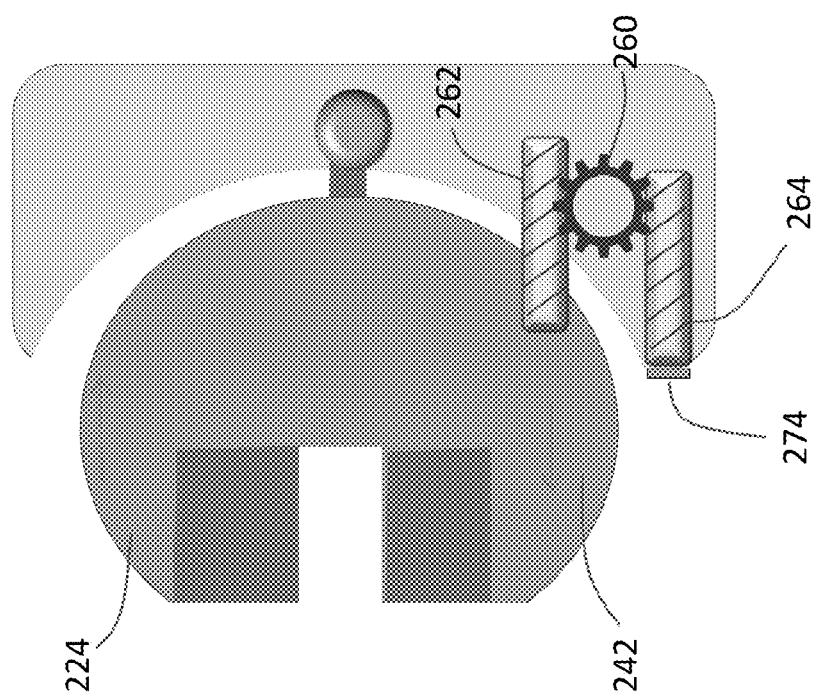

FIG. 12C shows a cross-sectional view of the orthodontic bracket 220 in the direction of the arrows on the line B-B of FIG. 12A. The screw 276, rods 290 and 292, and a gear 294 are used to move the right portion 246 of the pivotable module 224. The rod 290 has an end that extends to outside of the base 222 and is coupled to the screw 276. When the user turns the screw 276, the rod 290 is rotated, which drives the gear 294, which drives the rod 292 that in turn moves the right portion 246 of the pivotable module 224. This allows the pivotable module 224 to rotate about the vertical axis 238.

In some implementations, additional screws, rods, and gears are used to enable the user to manually drive the left portion 244 and the upper portion 240, similar to driving the right portion 246 and the lower portion 242, respectively.

Referring to FIG. 12D, in some implementations, an orthodontic bracket 370 similar to the e-Bracket 220 of FIGS. 9A and 9B can have a base 372 that has a vertical track 374 and a horizontal track 376. The node or ball 200 (connected to the pivotable module 224, FIG. 9B) can fit in the tracks 374 and 376. The base 372 includes a circular area 378 at the center of base to allow for free multi-directional force application before the node 200 enters the track 374 or 376. In this example, for the situations where the movements of the pivotable module 224 are small, the node 200 will remain in the circular area 378. The node 200 enters the track 374 or 376 when the movements of the pivotable module 224 are large.

Referring to FIGS. 9A, 9B, 13A, and 13B, a space 248 between the upper module 226 and the lower module 228 allows an arch wire 280 to pass through. When the pivotable module 224 pivots about the horizontal axis 236 or vertical axis 238, or rotates in a clockwise or counterclockwise direction, the upper module 226 and the lower module 228 exert force on the arch wire 280, and the reaction force from the arch wire 280 pushes back against the upper and lower modules 226, 228, generating a force that is applied to the tooth connected to the bracket 220. Depending on the pivotal or rotational movement of the pivotable module 224, the arch wire 280 can push back against the bracket in a variety of directions.

The bracket 220 may include an integrated circuit chip (e.g., 202 shown in FIG. 8). Each bracket can be assigned a unique identifier so that different brackets can be adjusted differently, enabling individual functionality to each of several e-Brackets mounted on the patient's teeth.

Referring to FIGS. 14A and 14B, in some implementations, the e-Bracket 220 can have a fixed or removable cover 261 that is used to ligate the arch wire 280 with the bracket slot. In some implementations, the base 222 includes an integrated circuit chip 283 that has circuitry for controlling the miniature motors that drive gear assemblies for pushing the upper portion 240, lower portion 242, left portion 244, and right portion 246 of the pivotable module 224. The integrated circuit chip 283 can communicate wirelessly to external devices, such as the reader 108 or the cell phone 110.

Figure 15B:
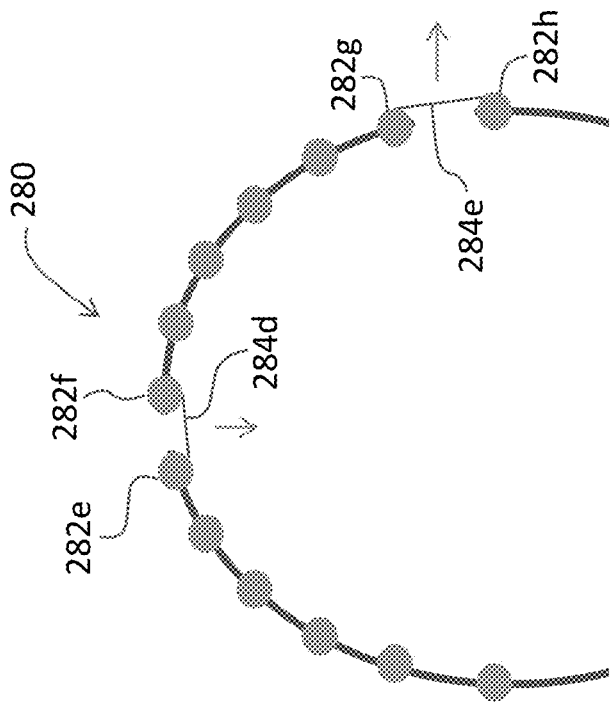
FIGS. 15A and 15B are diagrams of an exemplary e-Wire smart orthodontic wire.
Figure 15A:
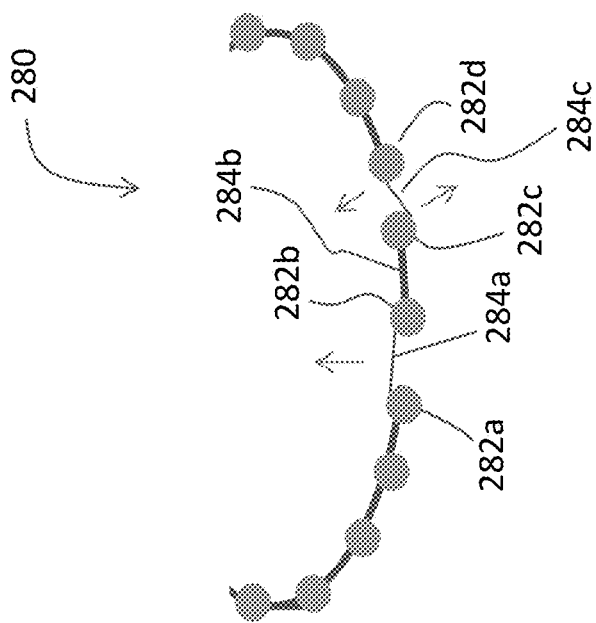

In some implementations, an arch wire is segmented into individual units (for each tooth) and interlinked via smart brackets, joints, or nodes that have the ability to revolve three-dimensionally to provide a detailed movement scheme for each tooth. FIG. 15A shows a front perspective view of an e-Wire smart orthodontic wire 280. FIG. 15B shows an upper view of the smart orthodontic wire 280. The smart orthodontic wire 280 includes smart nodes (e.g., 282a to 282d, collectively 282) and wire segments (e.g., 284a to 284c, collectively 284) between the nodes 282. Each smart node 282 can push or pull an adjacent wire segment in a forward, backward, upward, and/or downward direction with a twisting capability. In this document, depending on context, the smart nodes are also referred to as smart orthodontic brackets.

Two adjacent nodes can push the wire segment between the nodes in the same or different directions. For example, as shown in FIG. 15A, nodes 282a and 282b both push the wire segment 284a in an upward direction. The node 282c pushes one end of the wire segment 284c downward, while the node 282d pushes the other end of the wire segment 284c upward (known as a second order bend action). For example, as shown in FIG. 15B, nodes 282e and 282f both push the wire segment 284d in an inward direction. The nodes 282g and 282h both push the wire segment 284e in an outward direction (known as a first order bend action).

In some implementations, the wire segments 284 are coupled to orthodontic brackets similar to the way that an arch wire is attached to the orthodontic brackets. In other implementation the wire segments 284 can be directly bonded to the tooth surface. Because the nodes and wire segments are connected eventually to a tooth, the force that a node exerts against a wire segment will influence the tooth's final position. Furthermore, the system allows for spontaneous adjustment resulting from interactions between the nodes and the continuous arch wire configuration. For example, the force generated by the node 282a pulling the wire segment 284a may influence the force that is applied to the wire segment 284c, which is transferred to a corresponding bracket and its associated tooth.

Referring to FIG. 16, a smart node 282 has a wire segment attachment extending on each side that can be controlled independently to induce (along with the force provide by the adjacent node) a desired tooth movement. The positional corrections are performed through, e.g., wire twisting (root torque), opposite vertical movement (tilting), and opposite horizontal movement (rotational correction).

Referring to FIG. 17A, the smart node 282 includes a gear module that generates forces that are applied to archwire segments (e.g., 284a and 284b). The gear module can be driven manually or by miniature motors. The following describes examples in which the gear module is driven by miniature motors. In some implementations, the smart node 282 includes a first miniature motor 290 that generates a twisting force on a frame 298 that is connected to the wire segment 284b. The miniature motor 290 also generates a twisting force on a frame 300 that is connected to the wire segment 284a. When a single motor 290 is used, the twisting force applied to the frame 298 is the same as the twisting force applied to the frame 300. In some implementations, two motors can be used so that the twisting force applied to the frame 298 is independent of the twisting force applied to the frame 300, and the twisting force applied to the wire segment 284b is independent of the twisting force applied to the wire segment 284a. The motor 290 can, e.g., drive a transmission link 294 that is coupled to the frame 298, and drive a transmission link 296 that is coupled to the frame 300. Each of the transmission links 294 and 296 may include one or more miniature gears and/or miniature belts. Other ways of transferring the driving force from the motor to the frames 298, 300 can also be used.

A second motor 292 drives a rod 302 that pushes against the frame 300 to push the wire segment 284a inward or outward (i.e., in a direction into the mouth or in a direction out of the mouth). The motor 292 also drives a rod 304 that pushes against the frame 298 to push the wire segment 284b inward or outward. When two motors are used, the movement of the rod 302 is independent of the movement of the rod 304, so the inward or outward movements of the segments 284a and 284b can be independent of each other. A third motor (not shown in the figure) provides a force for rotating the node 282 or moving the rods 302 and 304 in directions perpendicular to those described above (e.g., producing upward and/or downward movements).

Figure 17B:
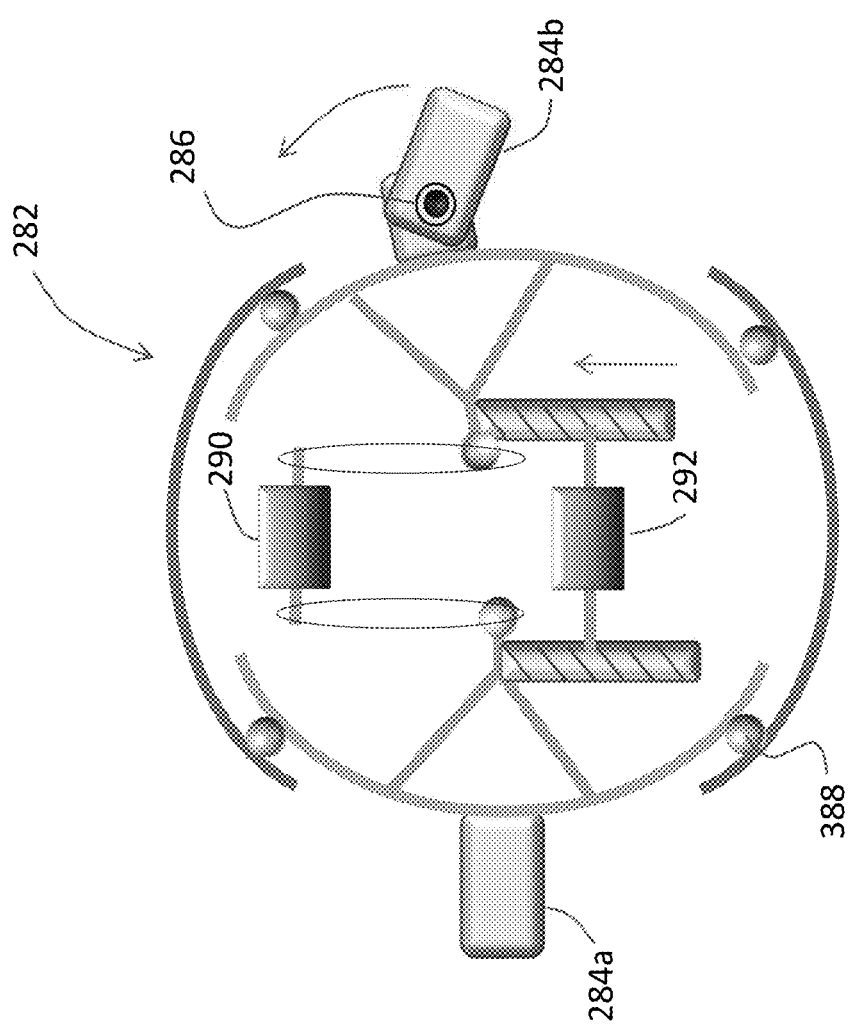

FIG. 17B shows a vertical cross-sectional view of the smart node 282 when the lower motor 292 is activated to achieve second-order action (i.e., tilting one end). The upper motor 290 when activated causes twisting action of the wire segment 284b (i.e., third-order action to cause root torquing or movement). In some implementations, a first end of the wire segment 284b is connected to a first smart node 282 via a rotational joint 286. A second end (not shown in the figure) of the wire segment 284b is connected to a second smart node (not shown in the figure) via another rotational joint. This allows the first smart node 282 and the second smart node to move independently even though the first smart node 282 and the second smart node are both joined to the same wire segment 284b. For example, the miniature motor 290 in the first smart node 282 may cause the first end of the wire segment 284b to move up (as shown in FIG. 17B), while the second smart node causes the second end of the wire segment 284b to move down (as shown in the example of FIG. 15A).

Figure 17C:
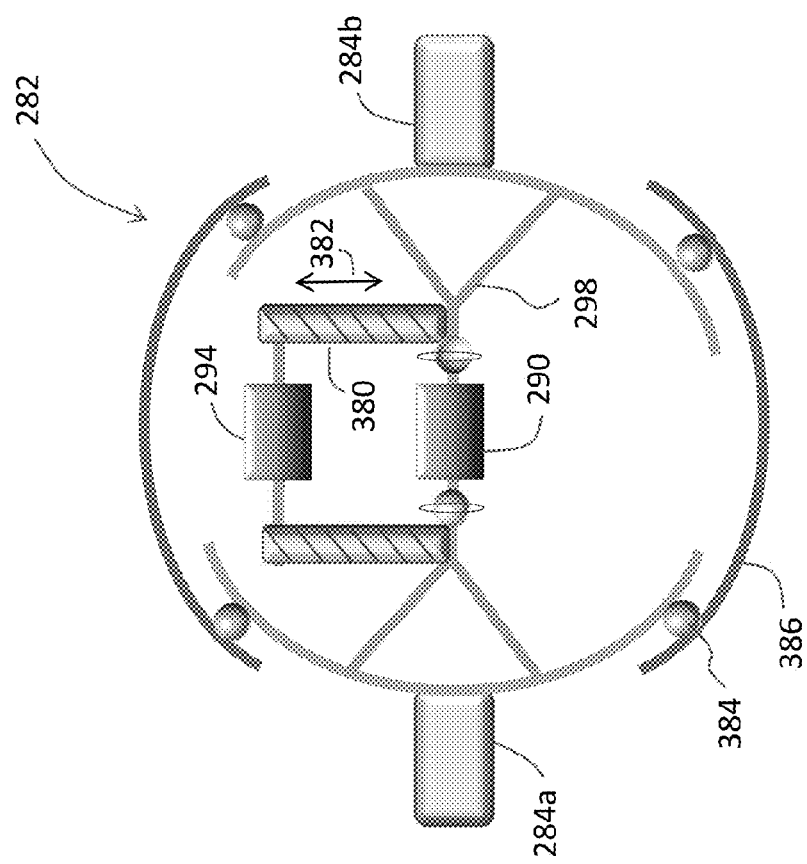

FIG. 17C shows a horizontal cross-sectional view of the smart node 282. A third motor 294 controls the in-out movement (first-order action) of the wire segments 284a and 284b. When the motor 294 drives a rod 380 to move along a direction 382, the rod 382 pushes the bracket 298 to cause the wire segment 284b to have a movement in the labial or lingual direction. In FIG. 17C, the motor 292 is below the motor 290 and is blocked from view. The smart node 282 includes four sliding metal balls 384 to enable the bracket 298 to slide against an outer frame 386. There are also four sliding metal balls 388 in the vertical cross-sectional view of FIG. 17B. Thus, in this example, there are a total of eight sliding metal balls.

Figure 17D:
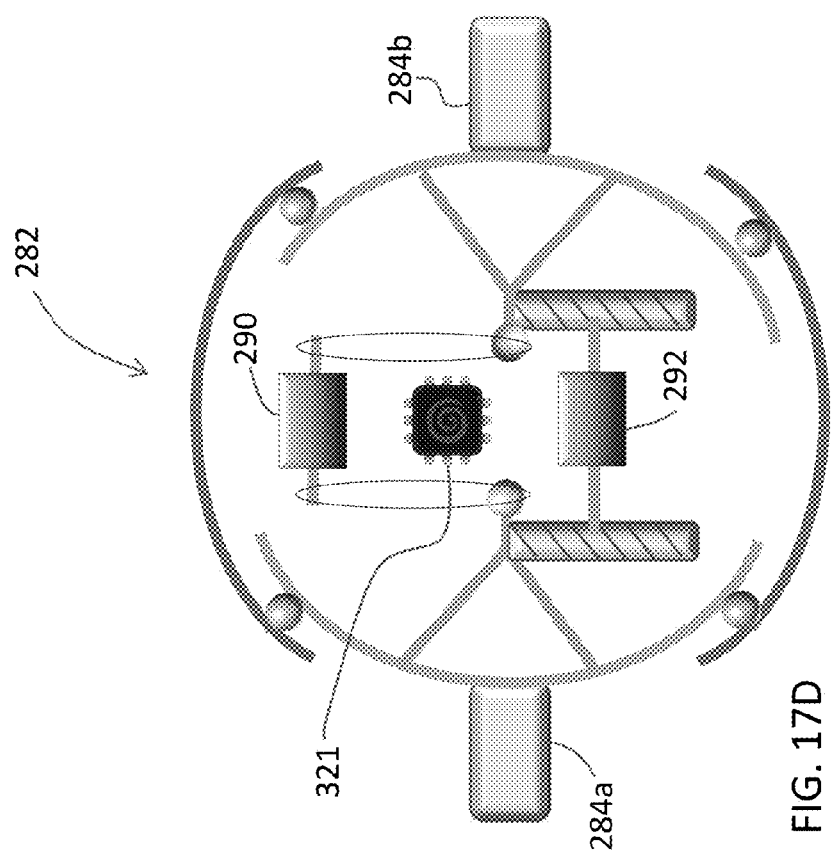

Referring to FIG. 17D, in some implementations, the smart node 282 includes an integrated circuit chip 321 that has circuitry for controlling the miniature motors (e.g., 290, 292, 294). The integrated circuit chip 321 has circuitry for communicating wirelessly to external devices, such as the reader 108 or the cell phone 110.

Figure 18:
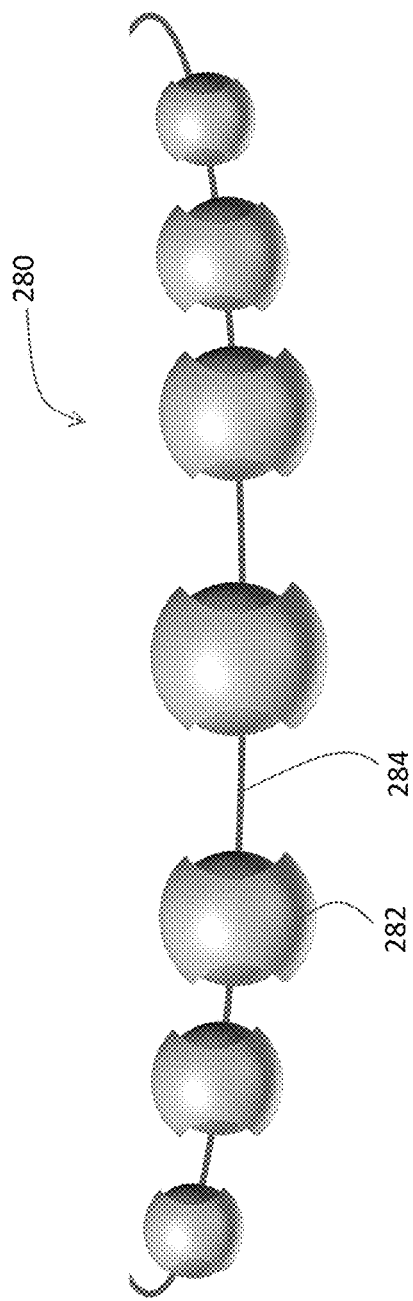
FIG. 18 shows a front view of the e-Wire smart orthodontic wire.
Figure 19:
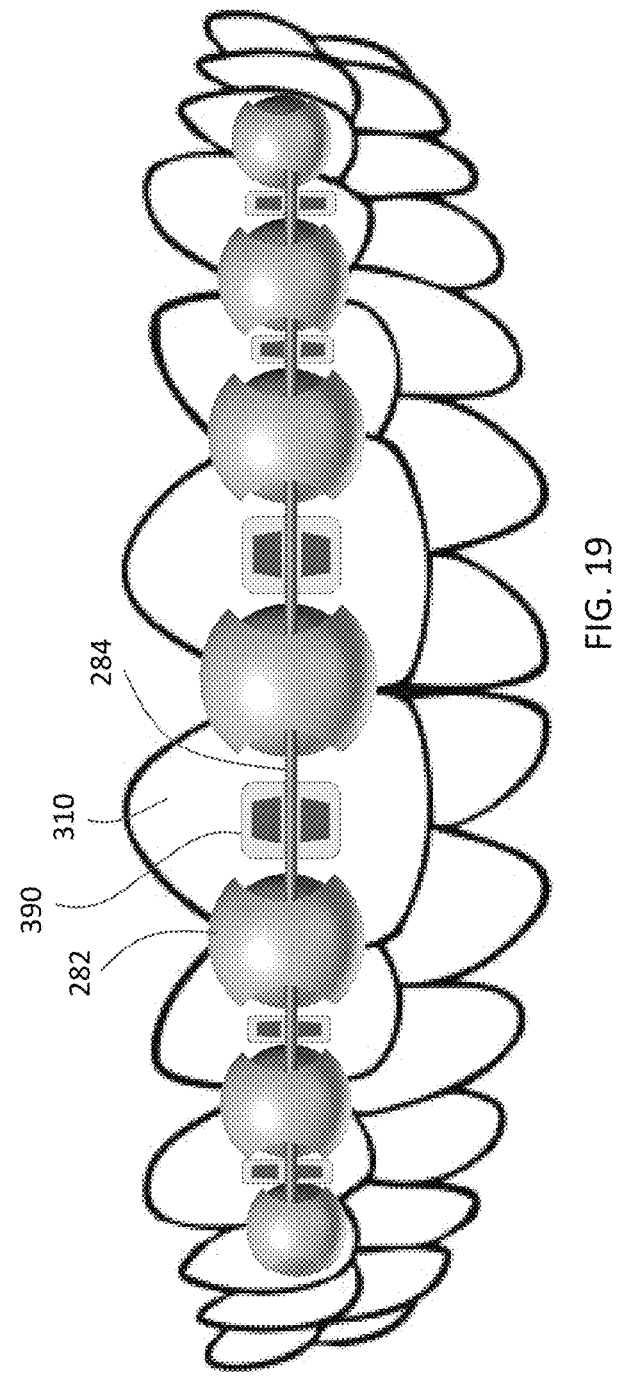
FIG. 19 shows a diagram of the position of the e-Wire smart orthodontic wire relative to a user's teeth.

FIG. 18 shows a front view of the e-Wire smart orthodontic wire 280. FIG. 19 shows the smart orthodontic wire 280 positioned relative to the teeth. In some examples, each of the wire segments 284 between two smart nodes 282 is coupled to a bracket 390 that is attached to a corresponding tooth 310. For example, the wire segment 284 can be inserted into an archwire slot of the bracket 390. The bracket 390 can be either a traditional orthodontic bracket or a smart bracket that can provide adjustable forces to the wire segment 284. In some examples, each of the wire segments 284 can be attached to the corresponding tooth by other interfaces, or by directly gluing the wire segment to a treated tooth surface.

Figure 21:
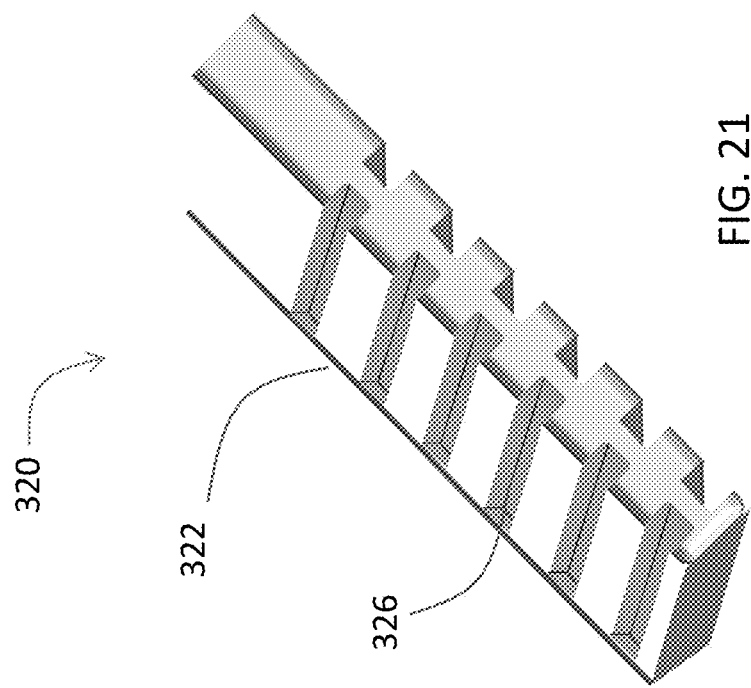
Figure 20:
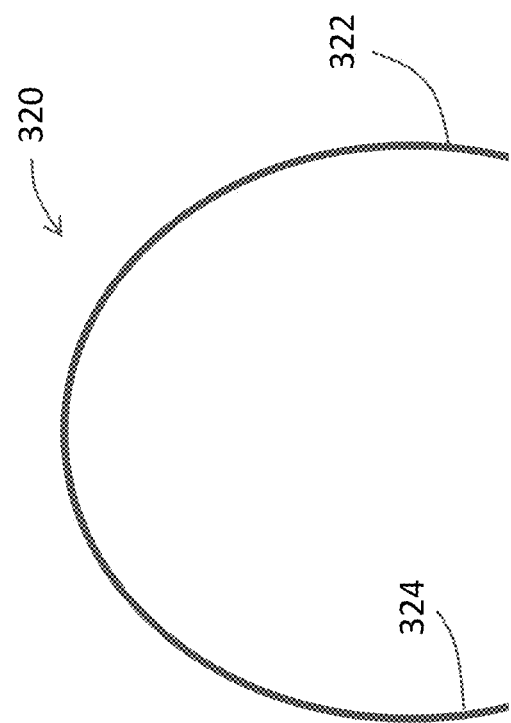

Referring to FIGS. 20 and 21, in some implementations, a tract arch wire 320 has a shape that is similar to a dental arch. Each end portion (322, 324) of the tract arch wire 320 has grooves or notches 326 that can be driven by gears. For example, a third of the arch wire 320 near one end can have grooves 326, and a third of the arch wire 320 near the other end can have grooves 326. The tract arch wire 320 can be used in combination with the e-Tract bracket 180 (FIGS. 7A, 7B, and 8). The tract arch wire 320 of FIGS. 20 and 21 can be the arch wire 196 of FIG. 8. For example, the tract arch wire 320 can be made of stainless steel alloy. For example, the arch wire 320 can be constructed to have a rectangular or round cross-sectional shape, with a width or diameter, respectively, ranging from, e.g., 0.016 inch by 0.022 inch to 0.021 inch by 0.027 inch ("full slot size"). The arch wire 320 can also have an elliptical cross-sectional shape. The arch wire 320 allows for "protracting" or "retracting" of the anterior teeth, hence the name "tract" arch wire.

Referring to FIGS. 22 and 23, in some implementations, a tract arch wire 330 has a main wire 338 and two branch wires 332 and 334. The main wire 338 is smooth and does not have any notch, whereas each of the branches 332 and 334 has notches 336 that can be pulled or pushed by gears. In this configuration, the tract arch wire 330 can be used with e-Tract brackets 180 that are mounted on mini-screw supporting implants placed gingivally to the teeth crown.

Figure 24:
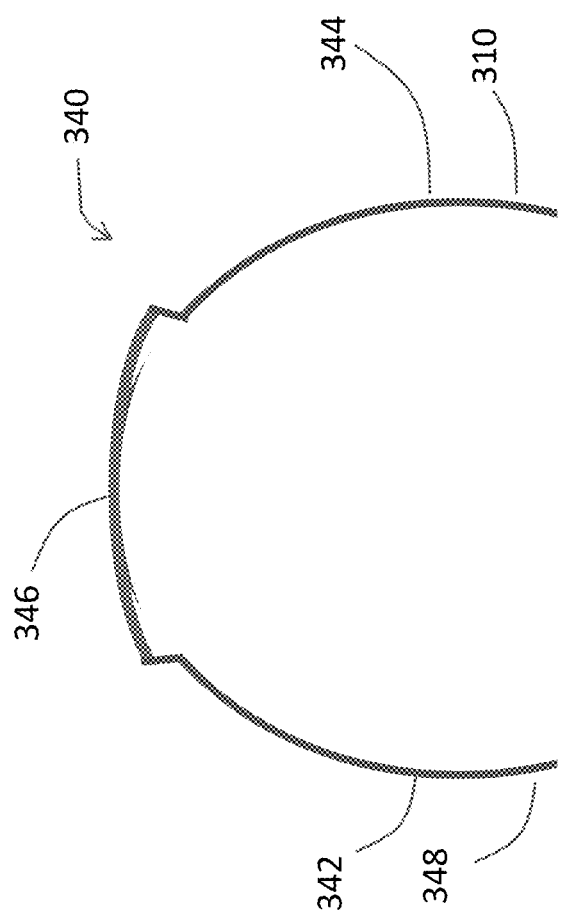
FIG. 24 is a diagram of a compensating arch wire.

Referring to FIG. 24, because the smart brackets, such as the e-Right bracket 122 (FIG. 4A), e-Tract bracket 180 (FIG. 7A), and the e-Bracket 220 (FIG. 9A), may be slightly thicker than conventional orthodontic brackets, it is useful to have a compensating arch wire 340 in which a portion 346 of the arch wire is offset from the rest of the arch wire. For example, the distance between the portion 346 of the arch wire to adjacent teeth is larger than the distance between a portion 342 or 344 of the arch wire to adjacent teeth. In some examples, the portion 346 of the arch wire coupled to smart brackets can be made of a material that is different from the other portions of the arch wire that are coupled to conventional brackets. In the example of FIG. 24, the smart brackets are used for anterior teeth. For example, a portion 348 near one end can have grooves 326, and a portion 310 near the other end can have grooves 326. The grooves 326 allow the use of e-Track brackets 124, 180 to protract or retract the anterior teeth.

Figure 25:
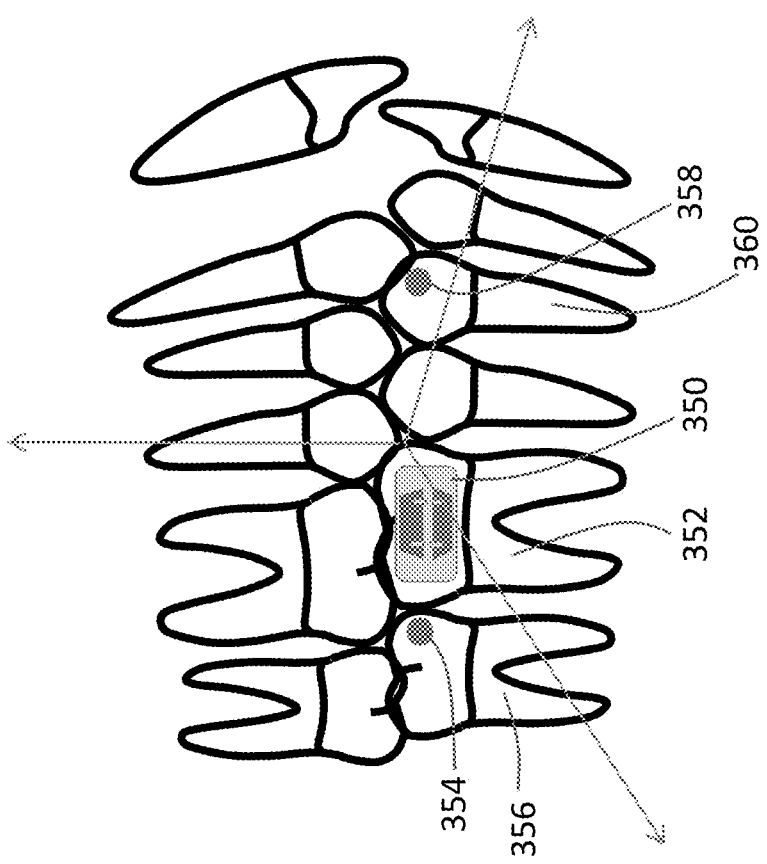
FIG. 25 is a diagram of a smart bracket and exemplary reference markers.

Various smart orthodontic brackets and wires have been described above. These smart brackets and wires can be used in the remote orthodontic system 100 of FIG. 1. Referring to FIG. 25, in order to monitor the movement of the tooth under treatment, markers can be attached to one or more adjacent teeth. For example, a smart bracket 350 is attached to a tooth 352 that needs to be aligned. A first marker 354 is attached to a tooth 356, and a second marker 358 is attached to another tooth 360. When the smart bracket 350 is first installed on the tooth 352, a set of one or more pictures of the teeth are taken. After a period of time, such as three or four weeks later, a second set of one or more pictures of the teeth are taken. The movement of the tooth 352 under treatment relative to the other teeth 356 and 360 can be measured by comparing the position of the bracket 350 relative to the markers 354 and 358 that function as reference points.

In some examples, the patient takes images of the teeth and sends them to the orthodontist, who monitors the progress of the treatment. If the movement of the tooth 352 is according to plan, then the smart bracket 350 will be adjusted according to plan. If the movement of the tooth 352 is outside of acceptable boundaries, then the orthodontist may adjust the treatment plan or ask the patient to return to the clinic for further examination and/or treatment. When the orthodontist needs to adjust the treatment plan, the orthodontist may send an instruction from the clinic terminal 106 to the server computer 104 to adjust the treatment plan stored locally at the server 104.

In some examples, the mobile phone 110 may execute an orthodontic app that provides instructions to the patient or a helper of the patient on how to take pictures in order to accurately determine the movement of the tooth 352. For example, a helper may use the camera on the mobile phone 110 to take pictures of the patient's teeth. A reference image that was previously taken can be overlaid on a live view taken by the phone camera. The reference image may show the two markers 354 and 358, so that the helper may position and orient the camera to take a picture of the teeth in which the markers 354 and 358 are at similar positions in the new picture. This makes it easier to compare the current picture with a previously taken picture to determine the movement of the tooth 352. A set of orthodontic biomechanical algorithms can be used by the system 100 to determine the auto adjustments to be made to the smart brackets, such as increasing or decreasing the forces applied by the gears in the e-Right brackets, e-Tract brackets, e-Brackets, or e-Wire arch wire.

The smart brackets may have sensors for sensing the force applied to the corresponding tooth. For example, a microelectromechanical sensor system having piezoresistive microsensors attached between the smart bracket and the tooth can be used to take measurements that can be used to calculate forces applied to the tooth in the x, y, and z directions, and moments in the x, y, and z directions. By monitoring the forces actually applied to the tooth, the system 100 can determine whether the motors in the smart brackets need to be adjusted to apply more or less force in a certain direction.

The chips (e.g., 174 of FIG. 6, 202 of FIG. 8, 283 of FIG. 14B, 321 of FIG. 17D), the miniature motors, and the sensors system can be powered wirelessly by beaming power to microcoils in the smart nodes. The chips may include circuitry for modulating data sent to the reader 108 or the server 104, or demodulating the signals received from the reader 108 or the server 104.

The remote orthodontic system 100 helps orthodontists and their patients to have a high quality orthodontic treatment, with reduced visits to the dental office and reduced costs. For example, the adjustments to the smart brackets and arch wires can be made while the patients are at home. The orthodontists can also monitor the treatments and make adjustments to the treatment plans from home, allowing more flexible work schedules.

Novel orthodontic brackets that can generate and deliver forces have been described above. The system 100 is interactive in which the patient and the treatment provider are able to monitor the status of teeth alignment and report responses and symptoms. The system can be remotely controlled, enabling quick re-adjustment and auto-correction. The system can apply biomechanical equations based on the known static and dynamic equilibrium laws and algorithms. The system provides treatments with predictable and improved outcomes, so the treatment duration can be accurately forecasted and better controlled.

Each of the computer server 104, mobile phone 110, and reader 108 can include one or more processors and one or more computer-readable mediums (e.g., RAM, ROM, SDRAM, hard disk, optical disk, and flash memory). The one or more processors can perform various calculations or control functions described above. The calculations and various functions can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., DRAM) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory (ROM) or a random access memory (RAM) or both. The essential elements of a computer are a processor for executing instructions and one or more memories for storing instructions and data. Generally, a computer will also include, or be operatively coupled to communicate with, one or more mass storage devices for storing data files. The mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, CD-R, DVD-ROM, DVD-R, Blu-ray DVD disks. The processor and the memory can be supplemented by, or incorporated in, ASICs (application-specific integrated circuits). The chips (e.g., 174 of FIG. 6, 202 of FIG. 8, 283 of FIG. 14B, 321 of FIG. 17D) may include one or more processors described above. The chips may also include one or more volatile or non-volatile memories for storing instructions to be executed by the one or more processors.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Other embodiments are within the scope of the following claims. For example, a combination of various types of smart brackets can be used for treating one patient. The smart brackets and arch wires can be made of materials different from those described above. In some implementations, each smart bracket can include a radio frequency identification tag associated with a unique identifier. In some implementations, each chip (e.g., 174 of FIG. 6, 202 of FIG. 8, 283 of FIG. 14B, 321 of FIG. 17D) has a unique identifier. This way, if a patient has multiple smart brackets, the server 104 can uniquely identify each smart bracket and send different instructions to different smart brackets. Each of the gears in the smart brackets or nodes can have a locking mechanism to prevent counter rotation after the gears have been driven in a certain direction. The locking mechanism can be controlled to be released when necessary to allow the gears to rotate in the opposite direction. In some examples, for the smart orthodontic wire 280 shown in FIGS. 15A and 15B, each wire segment can span more than one tooth so that the number of smart nodes can be reduced.

What is claimed is:

1. An orthodontic system, comprising:
   at least one orthodontic bracket configured to be attached to a surface of a tooth, the at least one orthodontic bracket defining an archwire slot, the at least one orthodontic bracket comprising
      a base configured to be attached to the surface of the tooth,
      a gear system that comprises a first gear,
      a motor to drive the gear system,
      an integrated circuit to control the motor,
      an archwire placed in the archwire slot, and
      a first member and a second member both attached to the base, the first and second members being spaced apart to define the archwire slot, wherein the first member comprises the first gear and a first rod, the first rod has a first portion having notches that engage the first gear, the first rod has a second portion that extends into the archwire slot, when the first gear rotates in a specified direction, the first gear drives the first rod in which the first rod is configured to contact the archwire and apply a first force to the archwire; and
   a computer server configured to send instructions to the integrated circuit in the at least one orthodontic bracket;
   wherein the integrated circuit is configured to control the motor according to the instructions from the computer server to drive the gear system to apply a force to the archwire.

2. The orthodontic system of claim 1 in which the gear system further comprises a second gear, and
   the second member comprises the second gear and a second rod, the second gear drives the second rod to apply a second force to the archwire.

3. The orthodontic system of claim 2 in which the first member comprises a third rod, the third rod has a first portion having notches that engage the first gear, the third rod has a second portion that extends into the archwire slot, the first and third rods engage opposing sides of the first gear such that when the first gear rotates, the first and third rods move in opposite directions in which one of the first and third rods extends further into the archwire slot while the other of the first and third rods extends less into the archwire slot.

4. The orthodontic system of claim 3 in which the second member comprises a fourth rod, the fourth rod has a first portion having notches that engage the second gear, the fourth rod has a second portion that extends into the archwire slot, the second and fourth rods engage opposing sides of the second gear such that when the second gear rotates, the second and fourth rods move in opposite directions in which one of the second and fourth rods extends further into the archwire slot while the other of the second and fourth rods extends less into the archwire slot.

5. The orthodontic system of claim 4 in which the first rod is positioned at a first distance from the base, the second rod is positioned at a second distance from the base, the third rod is positioned at a third distance from the base, the fourth rod is positioned at a fourth distance from the base, the first distance is different from the second distance, and the third distance is different from the fourth distance.

6. The orthodontic system of claim 5 in which the first distance is the same as the third distance, and the second distance is the same as the fourth distance.

7. The orthodontic system of claim 2 in which the first rod is positioned at a first distance from the base, the second rod is positioned at a second distance from the base, and the first distance is different from the second distance.

8. The orthodontic system of claim 1 in which the at least one orthodontic bracket comprises a wireless energy receiver to receive energy wirelessly for powering the motor.

9. The orthodontic system of claim 8, comprising an external wireless energy transmitter to transmit energy wirelessly to the wireless energy receiver.

10. The orthodontic system of claim 1, comprising a sensor to detect a force applied by the at least one orthodontic bracket to the tooth.

11. The orthodontic system of claim 10, comprising a wireless energy transfer module to receive energy wirelessly for powering the sensor.

12. The orthodontic system of claim 10 in which the computer server is configured to receive information from the sensor about the force applied by the at least one orthodontic bracket to the tooth, generate a second set of instructions based on the information received from the sensor, and send the second set of instructions to the integrated circuit to control the motor to drive the gear system to apply a second force to the archwire.

13. The orthodontic system of claim 1 in which the computer server is configured to receive information about a measured position of the tooth, compare the measured position of the tooth with a reference position of the tooth provided by a dental treatment plan, generate a second set of instructions based on the comparison, and send the second set of instructions to the integrated circuit to control the motor to drive the gear system to apply a second force to the archwire.

14. The orthodontic system of claim 1 in which the at least one orthodontic bracket comprises a cover attached to the first and second members, in which the cover is configured to retain the archwire within the archwire slot.

15. The orthodontic system of claim 1 in which the integrated circuit comprises a communication module to communicate wirelessly with the computer server.

16. The orthodontic system of claim 15 in which the integrated circuit is configured to receive instructions wirelessly and to control the motor according to the instructions.

17. The orthodontic system of claim 1 in which the at least one orthodontic bracket comprises a radio frequency identification tag associated with a unique identifier.

18. A method comprising:
attaching at least one orthodontic bracket to a surface of a tooth, the at least one orthodontic bracket defining an archwire slot, the at least one orthodontic bracket comprising
a base configured to be attached to the surface of the tooth,
a gear system that comprises a first gear,
a motor to drive the gear system,
an integrated circuit to control the motor, and
a first member and a second member both attached to the base, the first and second members being spaced apart to define the archwire slot, wherein the first member comprises the first gear and a first rod, the first rod has a first portion having notches that engage the first gear, the first rod has a second portion that extends into the archwire slot;
placing an archwire in the archwire slot; and
sending instructions to the integrated circuit in the at least one orthodontic bracket, in which the integrated circuit is configured to control the motor according to the instructions to cause the motor to drive the gear system to apply a first force to the archwire, including rotating the first gear to drive the first rod to contact the archwire and apply the first force to the archwire.

19. The method of claim 18
wherein attaching the at least one orthodontic bracket to the surface of the tooth comprises attaching the base of the at least one orthodontic bracket to the surface of the tooth.

20. The method of claim 19 in which the gear system comprises a second gear, the second member comprises the second gear and a second rod,
wherein the method comprises using the second gear to drive the second rod to apply a second force to the archwire.

21. The method of claim 18, comprising wirelessly transferring energy to the at least one orthodontic bracket to power the motor.

22. A method comprising:
receiving, using one or more processors, first information associated with a dental treatment plan;
generating, using the one or more processors, a first set of instructions based on the first information; and
sending, using the one or more processors, the first set of instructions wirelessly to an orthodontic bracket to cause the orthodontic bracket to apply a first prescribed force to a tooth according to the first set of instructions;
wherein the orthodontic bracket comprises
a base configured to be attached to the surface of the tooth,
a gear system that comprises a first gear,
a motor to drive the gear system,
an integrated circuit to control the motor,
an archwire placed in the archwire slot, and a first member and a second member both attached to the base, the first and second members being spaced apart to define the archwire slot, wherein the first member comprises the first gear and a first rod, the first rod has a first portion having notches that engage the first gear, the first rod has a second portion that extends into the archwire slot; and wherein the first set of instructions is configured to cause the first gear to rotate to drive the first rod to contact the archwire and apply the first prescribed force to the archwire.

23. The method of claim 22, comprising receiving second information associated with the dental treatment plan;
based on the second information, generating a second set of instructions; and
sending the second set of instructions wirelessly to the orthodontic bracket to cause the orthodontic bracket to apply a second prescribed force to the tooth according to the second set of instructions, in which the second prescribed force is different from the first prescribed force.

24. The method of claim 22, comprising:
receiving information about a measured position of the tooth;
comparing the measured position of the tooth with a reference position of the tooth;
generating a second set of instructions based on the comparison; and
sending the second set of instructions to the integrated circuit to control the motor to drive the gear system to apply a second force to the archwire.

25. The method of claim 22, comprising:
receiving information about a measured position of the tooth;
comparing the measured position of the tooth with a reference position of the tooth; and
generating a message if a difference between the measured position of the tooth and the reference position of the tooth is above a predetermined threshold.

26. A computer readable medium storing executable instructions that when executed by a computer causes the computer to:
receive first information regarding a dental treatment plan;
based on the first information, generate a first set of instructions; and
send the first set of instructions wirelessly to an orthodontic bracket to cause the orthodontic bracket to apply a first prescribed force to a tooth according to the first set of instructions;
wherein the orthodontic bracket comprises
a base configured to be attached to the surface of the tooth,
a gear system that comprises a first gear,
a motor to drive the gear system,
an integrated circuit to control the motor,
an archwire placed in the archwire slot, and
a first member and a second member both attached to the base, the first and second members being spaced apart to define the archwire slot, wherein the first member comprises the first gear and a first rod, the first rod has a first portion having notches that engage the first gear, the first rod has a second portion that extends into the archwire slot; and
wherein the first set of instructions is configured to cause the first gear to rotate to drive the first rod to contact the archwire and apply the first prescribed force to the archwire.

27. The computer readable medium of claim 26, in which the instructions when executed by the computer further causes the computer to:
receive second information associated with the dental treatment plan;
based on the second information, generate a second set of instructions; and
send the second set of instructions wirelessly to the orthodontic bracket to cause the orthodontic bracket to apply a second prescribed force to the tooth according to the second set of instructions, in which the second prescribed force is different from the first prescribed force.

28. The computer readable medium of claim 26, in which the instructions when executed by the computer further causes the computer to:
receive information about a measured position of the tooth;
compare the measured position of the tooth with a reference position of the tooth;
generate a second set of instructions based on the comparison; and
send the second set of instructions to the integrated circuit to control the motor to drive the gear system to apply a second force to the archwire.

29. The computer readable medium of claim 26, in which the instructions when executed by the computer further causes the computer to:
receive information about a measured position of the tooth;
compare the measured position of the tooth with a reference position of the tooth; and
generate a message if a difference between the measured position of the tooth and the reference position of the tooth is above a predetermined threshold.

* * * * *